US012609207B2

(12) United States Patent
Wilson et al.

(10) Patent No.: US 12,609,207 B2
(45) Date of Patent: Apr. 21, 2026

(54) PREDICTION OF STENT EXPANSION FOR TREATMENTS

(71) Applicants: Case Western Reserve University, Cleveland, OH (US); University Hospitals Cleveland Medical Center, Cleveland, OH (US); Florida Institute of Technology, Melbourne, FL (US); University of South Florida, Tampa, FL (US)

(72) Inventors: David L. Wilson, Cleveland Heights, OH (US); Yazan Gharaibeh, Shaker Heights, OH (US); Juhwan Lee, Westlake, OH (US); Sadeer Al-Kindi, Lyndhurst, OH (US); Vladislav N. Zimin, Beachwood, OH (US); Linxia Gu, Melbourne, FL (US); Pengfei Dong, Melbourne, FL (US); Hiram Bezerra, Tampa, FL (US)

(73) Assignees: Case Western Reserve University, Cleveland, OH (US); University Hospitals Cleveland Medical Center, Cleveland, OH (US); Florida Institute of Technology, Melbourne, FL (US); University of South Florida, Tampa, FL (US)

(*) Notice: Subject to any disclaimer, the term of this patent is extended or adjusted under 35 U.S.C. 154(b) by 568 days.

(21) Appl. No.: 18/150,315

(22) Filed: Jan. 5, 2023

(65) Prior Publication Data

US 2023/0223152 A1    Jul. 13, 2023

Related U.S. Application Data

(60) Provisional application No. 63/298,495, filed on Jan. 11, 2022.

(51) Int. Cl.
*G16H 50/50* (2018.01)
*A61B 5/00* (2006.01)
(Continued)

(52) U.S. Cl.
CPC ........... *G16H 50/50* (2018.01); *A61B 5/7264* (2013.01); *A61B 34/10* (2016.02); *G06T 7/0012* (2013.01);
(Continued)

(58) Field of Classification Search
CPC ........ G16H 20/40; G16H 30/40; G16H 50/20; G16H 50/30; G16H 50/50; G16H 50/70;
(Continued)

(56) References Cited

U.S. PATENT DOCUMENTS

| | | | |
|---|---|---|---|
| 2011/0071404 A1* | 3/2011 | Schmitt | A61B 5/02007 382/128 |
| 2012/0075638 A1* | 3/2012 | Rollins | A61B 1/3137 356/479 |

(Continued)

FOREIGN PATENT DOCUMENTS

CN        105243686 B    *    3/2011

OTHER PUBLICATIONS

Min et al., "Prediction of Coronary Stent Underexpansion by Pre-Procedural Intravascular Ultrasound-Based Deep Learning", JACC Cardiovasc Interv. May 10, 2021;14(9):1021-1029 (Year: 2021).*

(Continued)

*Primary Examiner* — Ping Y Hsieh
*Assistant Examiner* — Jose M Torres
(74) *Attorney, Agent, or Firm* — Eschweiler & Potashnik, LLC

(57) ABSTRACT
The present disclosure, in some embodiments, relates to a method of predicting stent expansion. The method includes
(Continued)

100

Access pre-stent intravascular image data of patient's blood vessel — 102

Segment pre-stent intravascular image data to identify lumen and calcification lesion(s) — 104

Extract plurality of features from lumen and/or calcification lesion(s) — 106

Apply regression model to plurality of features to determine post stent lumen areas and/or stent expansion metrics (SEMs) — 108

Identify minimum stent expansion metric (mSEM) from SEMs — 110

Classify blood vessel as well-expanded area or under-expanded area based upon mSEM — 112

Determine treatment plan for patient based upon classification — 114 accessing a pre-stent intravascular image of a blood vessel of a patient and segmenting the pre-stent intravascular image to identify a lumen and a calcification lesion. A plurality of features are extracted from one or more of the lumen and the calcification lesion. A regression model is applied to one or more of the plurality of features to determine a minimum stent expansion metric (mSEM). The mSEM indicating how much a stent will expand after implantation. The mSEM is used to generate a classification of the blood vessel as an under-expanded area or a well-expanded area.

20 Claims, 18 Drawing Sheets

(51) Int. Cl.

| | |
|---|---|
| *A61B 34/10* | (2016.01) |
| *G06T 7/00* | (2017.01) |
| *G16H 30/40* | (2018.01) |

(52) U.S. Cl.

CPC ........ *G16H 30/40* (2018.01); *A61B 2034/104* (2016.02); *G06T 2207/10101* (2013.01); *G06T 2207/20081* (2013.01); *G06T 2207/30096* (2013.01); *G06T 2207/30101* (2013.01)

(58) Field of Classification Search

CPC . A61B 5/0066; A61B 5/02007; A61B 5/6852; A61B 5/7264; A61B 5/7267; A61B 34/10; A61B 2034/104; G06T 7/0012; G06T 2207/10101; G06T 2207/20081; G06T 2207/30052; G06T 2207/30096; G06T 2207/30101; G06T 2207/30104; G06N 20/00

See application file for complete search history.

(56) References Cited

U.S. PATENT DOCUMENTS

| | | | | |
|---|---|---|---|---|
| 2012/0310611 | A1* | 12/2012 | Sadasivan | D04C 1/06 |
| | | | | 703/6 |
| 2016/0022208 | A1* | 1/2016 | Gopinath | A61B 5/02154 |
| | | | | 600/427 |
| 2017/0309018 | A1* | 10/2017 | Shalev | G06T 7/0012 |
| 2018/0085170 | A1* | 3/2018 | Gopinath | G16H 50/30 |
| 2018/0225830 | A1* | 8/2018 | Gopinath | G06T 7/13 |
| 2019/0038358 | A1* | 2/2019 | Yoneyama | A61B 34/10 |
| 2019/0099080 | A1* | 4/2019 | Kunio | A61B 5/0084 |
| 2020/0294659 | A1* | 9/2020 | Gopinath | G06F 3/0485 |
| 2020/0327664 | A1* | 10/2020 | Wilson | G06F 18/2431 |
| 2021/0125337 | A1* | 4/2021 | Wilson | G06N 3/045 |
| 2021/0153776 | A1* | 5/2021 | Minar | A61B 5/1076 |
| 2022/0277456 | A1* | 9/2022 | Woolf | G06V 10/764 |
| 2024/0112343 | A1* | 4/2024 | Kang | A61B 8/085 |
| 2024/0169524 | A1* | 5/2024 | Wilson | A61B 5/02007 |
| 2024/0281977 | A1* | 8/2024 | Woolf | G06T 5/40 |
| 2024/0374242 | A1* | 11/2024 | Merritt | A61B 5/0215 |

OTHER PUBLICATIONS

Dong et al., "Simulation-Driven Machine Learning for Predicting Stent Expansion in Calcified Coronary Artery", Appl Sci (Basel). Sep. 1, 2020; 10(17), pp. 1-16. (Year: 2020).*

Chen et al., Machine translation of CN105243686 obtained from Patent Translate EPO on May 6, 2025, pp. 1-14. (Year: 2025).*

Lee et al., "Fully automated plaque characterization in intravascular OCT images using hybrid convolutional and lumen morphology features", Scientific Reports (2020) 10:2596, pp. 1-13. (Year: 2020).*

Kyriakidis et al., "A novel methodology for detection of lumen, outer wall, plaques and stent struts in coronary arteries using optical coherence tomography", 2019 IEEE 19th International Conference on Bioinformatics and Bioengineering (BIBE), pp. 697-701. (Year: 2019).*

* cited by examiner

100 ⟍

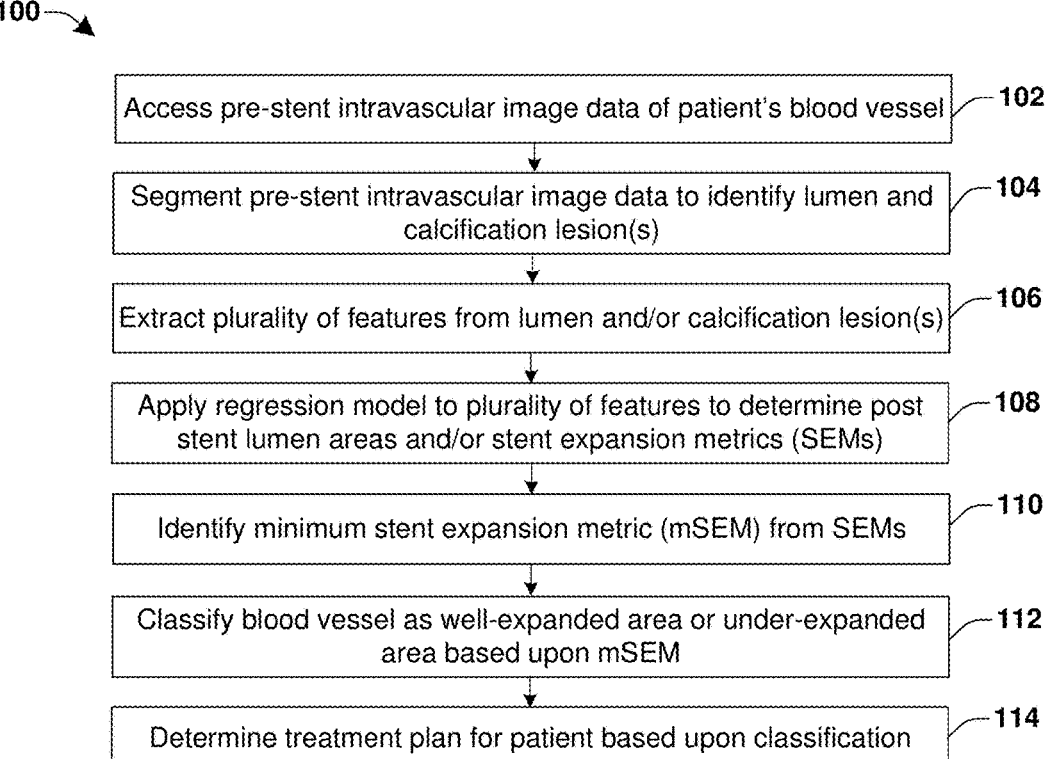

| Access pre-stent intravascular image data of patient's blood vessel | 102 |

| Segment pre-stent intravascular image data to identify lumen and calcification lesion(s) | 104 |

| Extract plurality of features from lumen and/or calcification lesion(s) | 106 |

| Apply regression model to plurality of features to determine post stent lumen areas and/or stent expansion metrics (SEMs) | 108 |

| Identify minimum stent expansion metric (mSEM) from SEMs | 110 |

| Classify blood vessel as well-expanded area or under-expanded area based upon mSEM | 112 |

| Determine treatment plan for patient based upon classification | 114 |

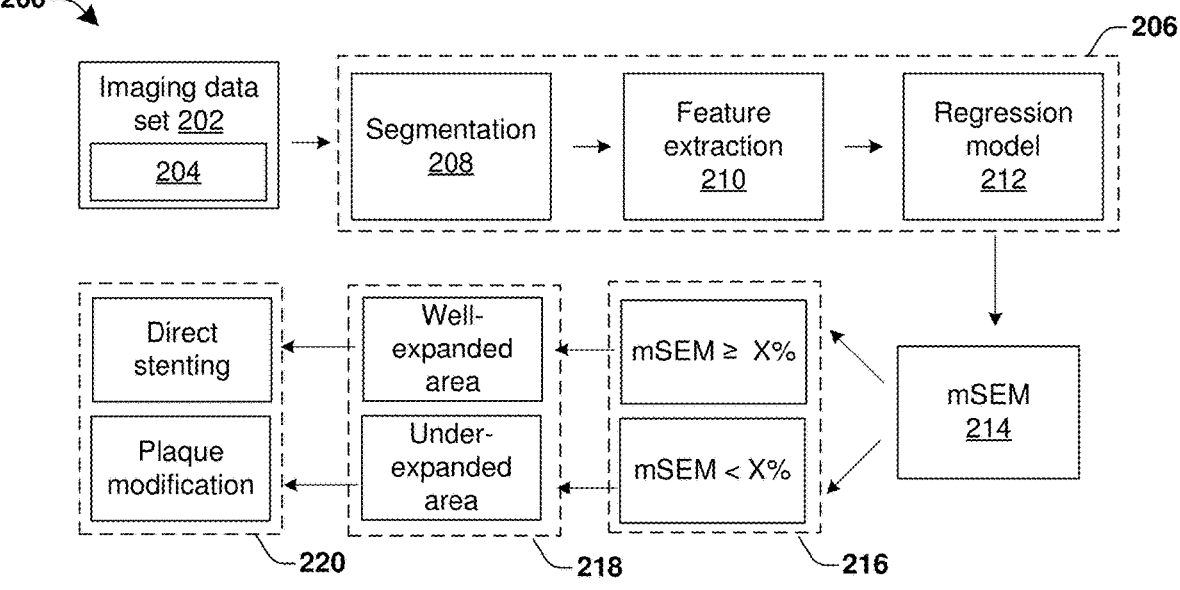

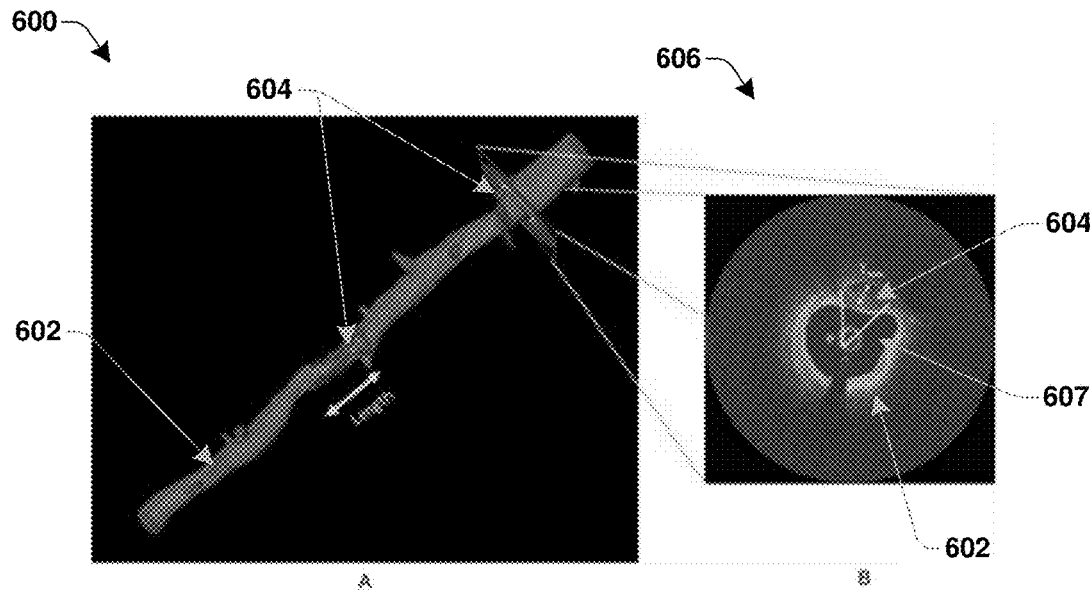

| Lumen features | | Calcification features | | Statistics |
|---|---|---|---|---|
| 2D features (Frame-based) | 3D features (Lesion-based) | 2D features (Frame-based) | 3D features (Lesion-based) | |
| Area | Volume | Max arc angle | Volume | Mean |
| %Area of Stenosis | Equivalent diameter | Max thickness | Volume index | Median |
| Major axis length | Extent | Max depth | Length | SD |
| Minor axis length | Convex volume | Area | Equivalent diameter | Max |
| Perimeter | Solidity | Major axis length | Extent | Min |
| Extent | Surface area | Minor axis length | Convex volume | Skewness |
| Eccentricity | | Extent | Solidity | Kurtoses |
| Solidity | | Eccentricity | Surface area | |
| Circularity | | Perimeter | Number of deposits | |
| Area < 0.5*Ref | | Solidity | Calcification % | |
| Area < 0.7*Ref | | Circularity | | |
| Area < 0.9*Ref | | Stretch ratios | | |

800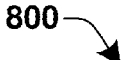
| Metric | Frame-based | Segmental analysis | Lesion-based |
|---|---|---|---|
| | 810 | 812 | 814 |
| 802 Accuracy | 0.78 ± 0.04 | 0.84 ± 0.04 | 0.71 ± 0.01 |
| 804 Sensitivity | 0.81 ± 0.06 | 0.87 ± 0.05 | 0.75 ± 0.01 |
| 806 Specificity | 0.75 ± 0.06 | 0.82 ± 0.05 | 0.68 ± 0.02 |
| 808 AUC | 0.79 ± 0.04 | 0.85 ± 0.02 | 0.73 ± 0.02 |
Fig. 8A
816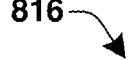
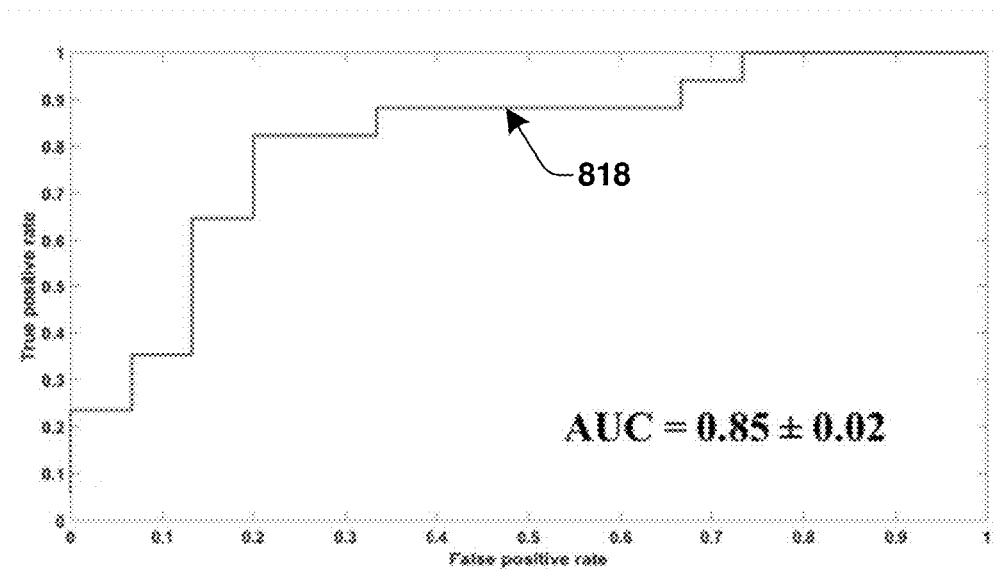
Fig. 8B

1100

| # | Tissue | Texture | Statistic | # | Tissue | Texture | Statistic |
|---|---|---|---|---|---|---|---|
| 1 | Calcification | Angle | Mean | 11 | Calcification | Thick | Median |
| 2 | Lumen | Area | Mean | 12 | Calcification | Depth | Mean |
| 3 | Lumen | % AS | Median | 13 | Calcification | Thick | SD |
| 4 | Lumen | % AS | Mean | 14 | Lumen | Volume | - |
| 5 | Calcification | Area | Mean | 15 | Calcification | Depth | Median |
| 6 | Calcification | Angle | SD | 16 | Calcification | Thick | Mean |
| 7 | Lumen | % AS | SD | 17 | Calcification | Angle | Median |
| 8 | Calcification | % | - | 18 | Calcification | Area | Median |
| 9 | Calcification | Area | SD | 19 | Calcification | Volume | - |
| 10 | Lumen | Area | SD | 20 | Calcification | Depth | SD |

Fig. 11A

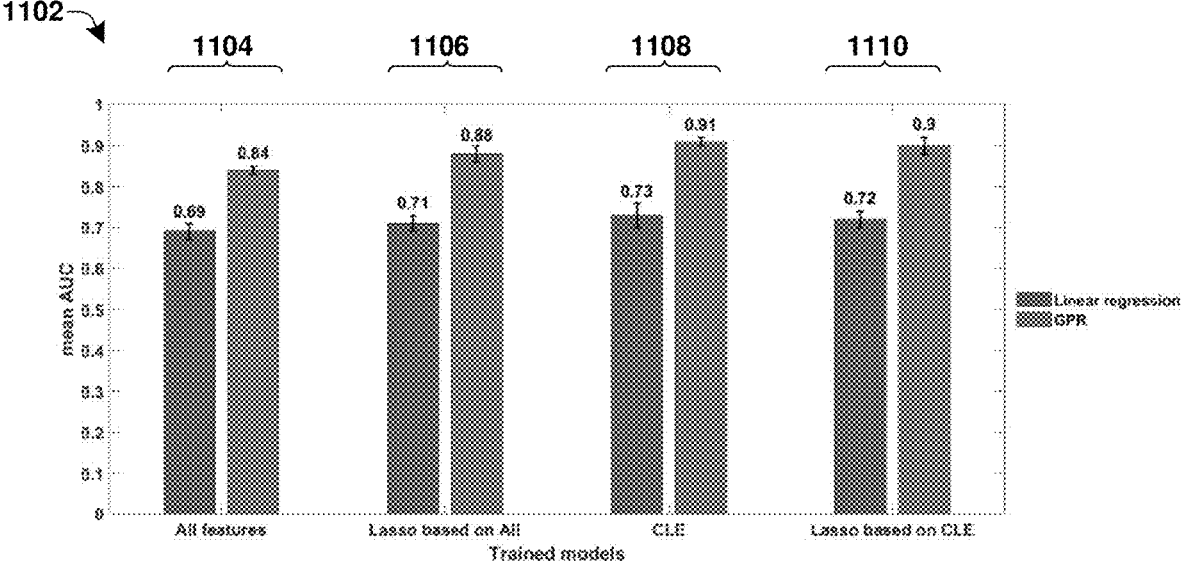

Fig. 11B

| | 810 | 812 | 814 | 1310 |
|---|---|---|---|---|
| Metric | Frame-based | Segmental analysis | Lesion-based | Lesion-based with CP |
| Accuracy | 0.78 ± 0.04 | 0.84 ± 0.04 | 0.71 ± 0.01 | 0.75 ± 0.02 |
| Sensitivity | 0.81 ± 0.06 | 0.87 ± 0.05 | 0.75 ± 0.01 | 0.75 ± 0.02 |
| Specificity | 0.75 ± 0.06 | 0.82 ± 0.05 | 0.68 ± 0.02 | 0.75 ± 0.01 |
| AUC | 0.79 ± 0.04 | 0.85 ± 0.02 | 0.73 ± 0.02 | 0.76 ± 0.02 |

1400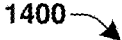

| |
| --- |
| Form/provide imaging data set with plurality of pre-stent intravascular images and post-stent intravascular images from plurality of patients ⌐1402 |

↓

| |
| --- |
| Separate imaging data set into one or more training set(s) and one or more test set(s) ⌐1404 |

↓

Train machine learning pipeline to generate minimum stent expansion metric (mSEM) from features extracted from pre-stent intravascular images Perform segmentation to identify lumen and calcification lesion(s) within pre-stent intravascular images in training set(s) ⌐1408

↓

Extract plurality of features from lumen and/or one or more calcifications ⌐1410

↓

Identify predictive features from plurality of features ⌐1412

↓

Train regression model to predictive features to determine post-stent lumen areas and/or stent expansion metrics (SEMs) ⌐1414

↓

Identify mSEM from the SEMs ⌐1416

1406

↓

| |
| --- |
| Validate regression model within test set(s) ⌐1418 |

↓

| |
| --- |
| Validate mSEM of regression model against actual mSEM ⌐1420 |

Fig. 14

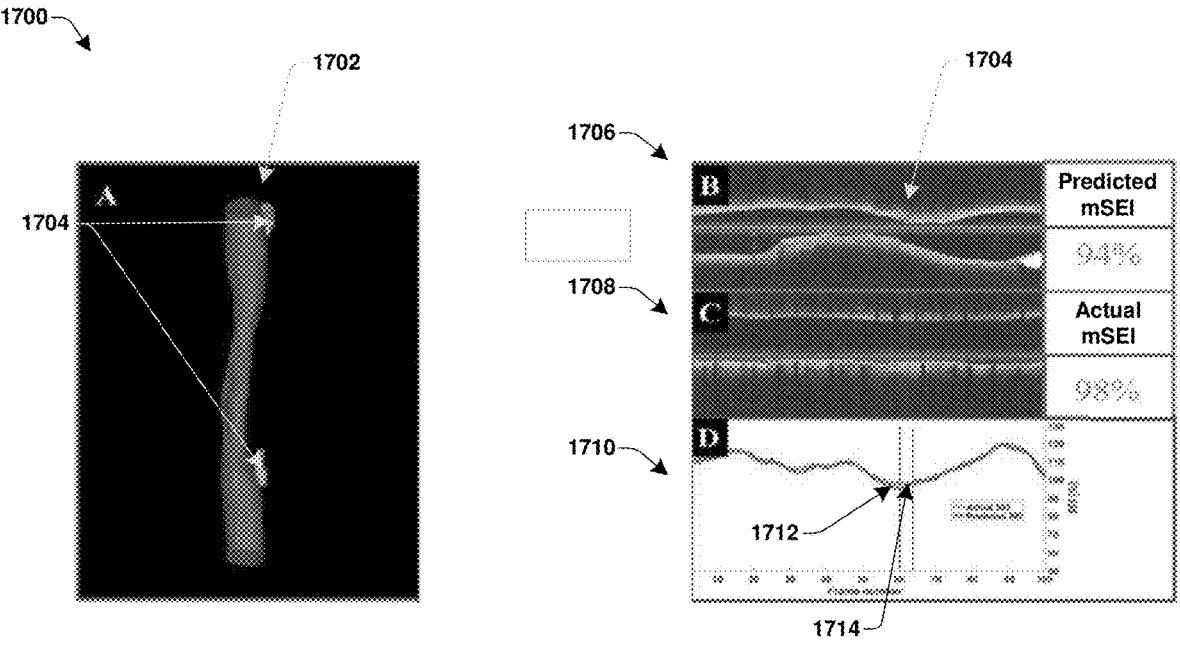
Fig. 17A                       Fig. 17B

1800

PREDICTION OF STENT EXPANSION FOR TREATMENTS

REFERENCE TO RELATED APPLICATION

This application claims the benefit of U.S. Provisional Application No. 63/298,495, filed on Jan. 11, 2022, the contents of which are hereby incorporated by reference in their entirety.

FEDERAL FUNDING NOTICE

This invention was made with government support under HL143484 awarded by the National Institutes of Health. The government has certain rights in the invention.

BACKGROUND

Calcification is the accumulation of calcium salts in a body tissue. It normally occurs in the formation of bone, but calcium can also be deposited abnormally in soft tissue. For example, calcium containing plaque can collect in the heart's two main arteries (e.g., coronary arteries), making it difficult for blood to travel through the arteries. The build-up of plaque in the coronary arteries is one of the strongest indicators for complications such as heart attacks, strokes, etc.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 1 illustrates some embodiments of a method of determining a treatment plan from a minimum stent expansion metric (mSEM) generated from a pre-stent intravascular image.

FIG. 2 illustrates some embodiments of a block diagram corresponding to a method and/or apparatus configured to determine a treatment plan from a mSEM generated from a pre-stent intravascular image.

FIG. 6A illustrates some embodiments showing exemplary features associated with calcification lesions within a blood vessel.

FIG. 6B illustrates some embodiments of a table showing a list of features that may be extracted from a lumen and/or from calcification lesions of a blood vessel.

FIG. 8A illustrates a table showing exemplary performance metrics corresponding to a disclosed regression model trained using different feature extraction approaches.

FIG. 8B illustrates some embodiments of a receiver operating characteristic (ROC) curve for a Gaussian Process Regression (GPR) algorithm configured to generate a mSEM for a pre-stent intravascular image.

FIG. 11A illustrates a table showing some embodiments of exemplary features of a calcification lesion expansion (CLE) group.

FIG. 11B illustrates some embodiments of bar graphs showing an AUC of a disclosed regression model trained by different groups of features.

FIG. 14 illustrates some additional embodiments of a method of generating a machine learning model that is configured to generate a mSEM from a pre-stent intravascular image.

FIGS. 17A-17B illustrate some embodiments of a comparison between a predicted mSEI and an actual mSEI of a well-expanded stent area.

DETAILED DESCRIPTION

Figure 3:
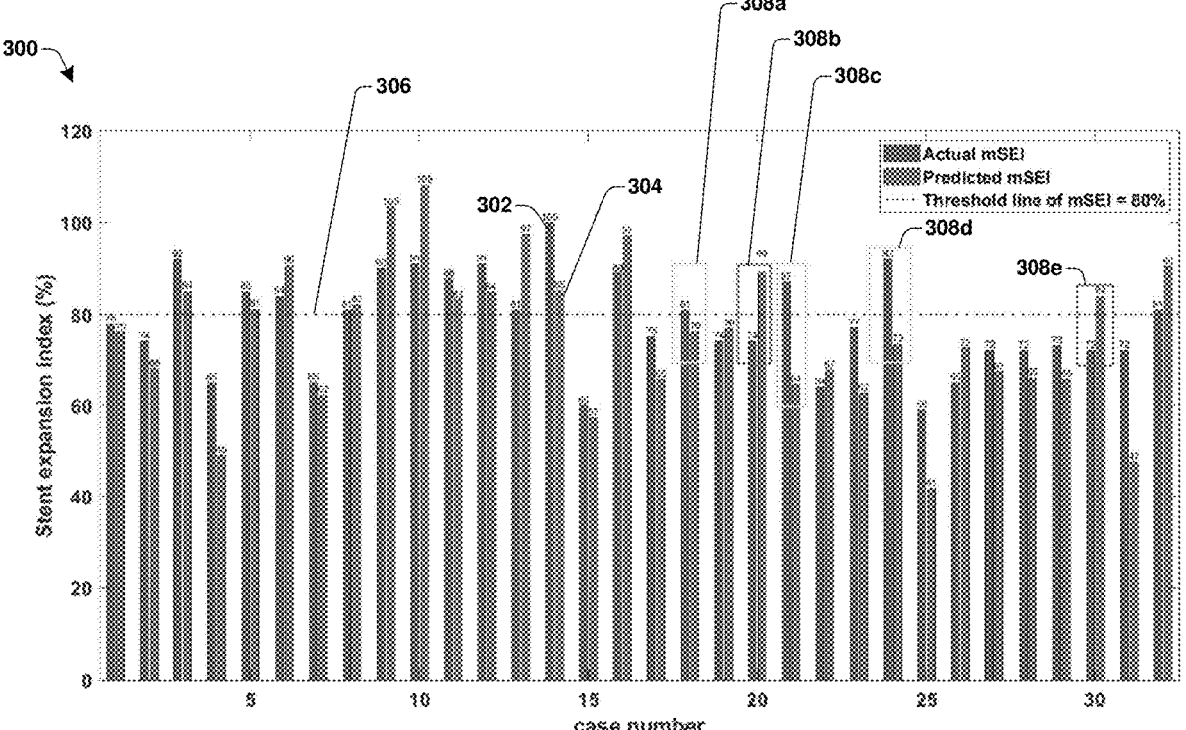
FIG. 3 illustrates some embodiments of a graph showing a comparison of minimum stent expansion indices (mSEls) generated by the disclosed method and actual stent expansion indices measured after insertion of stents.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Arteries are blood vessels that carry blood throughout your body. Healthy arteries have smooth inner walls and blood flows through them easily. However, over time, plaque can build up on the inner walls of arteries. Plaque is a waxy substance that includes fatty substances, cholesterol, calcium, waste products from cells, and blood-clotting material known as fibrin. Plaque buildup can clog arteries, thereby reducing blood flow through the arteries or, in some instances, blocking it altogether. Clogged arteries greatly increase a likelihood of heart attack, stroke, and/or death.

A healthy lifestyle is important to prevent and/or manage clogged arteries. However, sometimes lifestyle choices and/or medications are not sufficient to prevent plaque buildup. In such cases, surgical procedures may be used to treat a patient. One common surgical procedure used to treat plaque buildup is stent placement. A stent is a small tube-like structure that may be placed in an artery to maintain adequate blood flow through the artery. However, stent placement is not always successful. It has been appreciated that calcification lesions within a blood vessel may be a cause of stent placement failure, as calcification lesions may impair device delivery and/or inhibit stent expansion.

For example, once a stent is deployed in atherosclerotic tissue that is highly resistant to dilation (e.g., atherosclerotic tissue that has hardened due to the presence of calcification lesions), it is often tricky to fully expand the implanted stent, even using a noncompliant balloon (e.g., a high-pressure balloon). Because of the resistance to dilation, some stents may not expand as expected, leading to stent under-expansion (e.g., an area of a blood vessel in which a stent does not expand as expected) that results in an artery that is narrower than expected. Patients with stent under-expansion are at high risk for adverse outcomes, including stent thrombosis and in-stent restenosis, which can lead to acute coronary syndromes and, in the worst-case scenario, sudden cardiac death. Despite substantial improvements made in interventional procedures, stent design, drugs, and polymers as well as the adoption of therapeutic strategies, acute stent thrombosis and in-stent restenosis remain critical issues.

In some embodiments, the present disclosure provides a fully automated method (e.g., a machine learning method) to predict stent under-expansion from a pre-stent intravascular image (e.g., intravascular optical coherence tomography (IVOCT) images). The method comprises accessing a pre-stent intravascular image of a blood vessel (e.g., artery) of a patient. The pre-stent intravascular image is segmented to identify a lumen and one or more calcification lesions. A plurality of features are extracted from the lumen and/or the one or more calcification lesions. A regression model is applied to one or more of the plurality of features to determine a minimum stent expansion metric (mSEM), which indicates how much a stent will expand after implantation. The mSEM is used to classify the blood vessel as an under-expanded area (e.g., an area that will not allow for sufficient stent expansion to avoid complications) or a well-expanded area (e.g., an area that will allow for sufficient stent expansion to avoid complications).

The disclosed method provides excellent prediction of stent expansion (e.g., sensitivity of 0.87 and an area under the curve of 0.85) and therefore may play a fundamental role in the clinical management of patients, with implications regarding the choice of optimal medical therapy. For example, the ability to classify a blood vessel as an under-expanded area or a well-expanded area may allow a health care professional to determine if a treatment plan should include stenting and/or alternative plaque modification techniques.

FIG. 1 illustrates some embodiments of a method 100 of determining a treatment plan from a minimum stent expansion metric (mSEM) generated from a pre-stent intravascular image.

While the disclosed methods (e.g., methods 100, 1400, and 1800) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 102, pre-stent intravascular image data of a blood vessel (e.g., artery) of a patient is accessed. In some embodiments, the pre-stent intravascular image data is a pre-stent intravascular image (e.g., an optical coherence tomography (IVOCT) image) of a patient's blood vessel.

At act 104, the pre-stent intravascular image is segmented to identify a lumen and one or more calcification lesions.

At act 106, a plurality of features are extracted from the lumen and/or from the one or more calcification lesions.

At act 108, a regression model is applied to the plurality of features to determine post stent lumen areas and/or stent expansion metrics (SEMs). In some embodiments, the regression model may determine a plurality of SEMs respectively corresponding to frames of the pre-stent intravascular image that extend along the patient's blood vessel. In some embodiments, the plurality of SEMs may comprise a stent expansion index (SEI) that is a ratio of a post-lumen area of the blood vessel and a reference area of the blood vessel (e.g., an area associated with one or more parts of the blood vessel that are substantially free of calcification lesions).

At act 110, a minimum stent expansion metric (mSEM) is identified from the SEMs.

At act 112, the blood vessel is classified as a well-expanded area or an under-expanded area based upon the mSEM. Classification of the blood vessel as an under-expanded area means that a stent that is inserted into the blood vessel will likely not fully expand (e.g., expand to an expected and/or desired diameter), thereby potentially leading to complications such as stent thrombosis, in-stent restenosis, or the like. Classification of the blood vessel as a well-expanded area means that a stent that is inserted into the blood vessel will expand to a diameter that will not likely lead to complications such as stent thrombosis, in-stent restenosis, or the like.

At act 114, a treatment plan may be determined for the patient based upon the classification. If the blood vessel is classified as a well-expanded area, then the treatment plan may comprise and/or be insertion of a stent. Alternatively, if the blood vessel is classified as an under-expanded area, the treatment plan may comprise a plaque modification strategy (e.g., atherectomy, scoring/cutting balloon, shockwave, and/or using very high balloon pressures).

By generating a treatment plan based upon a mSEM that is determined from pre-stent intravascular image data, a health care provider is able to get a good idea of whether a stent insertion will be successful prior to insertion into a blood vessel. This is valuable to the health care profession and/or a patient since once a stent is implanted, it may be extremely difficult to go back and apply a procedure (e.g., orbital-atherectomy) to modify the plaque within the blood vessel.

FIG. 2 illustrates some embodiments of a block diagram 200 corresponding to a method and/or apparatus configured to determine a treatment plan from a mSEM generated from a pre-stent intravascular image.

As shown in the block diagram 200, an imaging data set 202 is formed and/or provided. The imaging data set 202 comprises one or more pre-stent intravascular images 204 of one or more blood vessels (e.g., arteries). In some embodiments, the one or more pre-stent intravascular images 204 may comprise a pre-stent intravascular optical coherence tomography (IVOCT) image generated by an IVOCT imaging system. Unlike an intravascular ultrasound tool, an IVOCT imaging system can penetrate calcification lesions to visualize their thickness, thereby allowing for a more complete assessment of the calcification lesions. Furthermore, the IVOCT imaging system is able to provide a detailed evaluation of a morphology of the calcifications and/or stent deployment (e.g., stent expansions, malapposition, stent edge dissection, or the like). Therefore, IVOCT images are a useful tool for identifying lesion severity, reference vessel size, lesion length, an extent of calcification, etc., in comparison with other imaging options (e.g., angiographic imaging).

The one or more pre-stent intravascular images 204 are provided to a machine learning pipeline 206 that is configured to apply one or more machine learning models to the one or more pre-stent intravascular images 204 to determine a minimum stent expansion metric (mSEM) 214 of a blood vessel of a patient. In some embodiments, the machine learning pipeline 206 comprises a segmentation stage 208, a feature extraction stage 210, and a regression model 212.

The segmentation stage 208 is configured to segment the one or more pre-stent intravascular images 204 to identify a lumen of the blood vessel and one or more calcification lesions within the blood vessel. In some embodiments, the segmentation stage 208 may utilize a deep learning-based segmentation method to identify the lumen and/or the one or more calcification lesions. In some embodiments, the segmentation stage 208 may be configured to utilize a deconvolution algorithm to identify the lumen and/or the one or more calcification lesions.

The feature extraction stage 210 is configured to extract a plurality of features from the lumen and/or the one or more calcification lesions. In various embodiments, the feature extraction stage 210 may extract the plurality of features from the lumen, from the one or more calcification lesions, and/or from both the lumen and the one or more calcification lesions within respective ones of the one or more pre-stent intravascular images 204. In some embodiments, the plurality of features may comprise two-dimensional (2D) lumen features (e.g., 2D features extracted from the lumen), three-dimensional (3D) lumen features (e.g., 3D features extracted from the lumen), 2D calcification features (e.g., 2D features extracted from the one or more calcification lesions), and/or three-dimensional (3D) calcification features (e.g., 3D features extracted from the one or more calcification lesions). In some embodiments, the use of a pre-stent IVOCT image allows for the feature extraction stage 210 to more accurately extract features, thereby leading to improved results over other types of pre-stent images.

The regression model 212 is applied to the plurality of features to generate the mSEM 214 of the blood vessel. In some embodiments, the mSEM may comprise a minimum stent expansion index (mSEI), a minimum expansion index (mEI) (e.g., which takes into account side branches extending off of a blood vessel that tend to reduce a reference area of the blood vessel), or the like. In some embodiments, the regression model 212 may comprise a linear regression (LR) model, a Gaussian process regression (GPR) algorithm, or the like.

In some embodiments, a mSEI may be generated by utilizing the regression model 212 to determine post-stent lumen areas at different locations (e.g., different frames) along the blood vessel. A plurality of stent expansion indices (SEIs) are subsequently determined from the post-stent lumen areas. In some embodiments, the plurality of SEIs may respectively be a ratio of a post-stent lumen area of a blood vessel and a reference area of the blood vessel (e.g., an area associated with one or more parts of the blood vessel that are substantially free of calcification lesions). In some embodiments, the plurality of SEIs are determined for each frame of a pre-stent intravascular image (e.g., a first SEI is determined for a first frame of a blood vessel, a second SEI is determined for a second frame of a blood vessel, etc.) by dividing a post-stent lumen area of a blood vessel for a frame by the reference area of the blood vessel. The mSEI is a smallest (e.g., minimum) one of the plurality of SEIs (e.g., the mSEI is a smallest ratio of the post-stent lumen area and the reference area of the blood vessel).

The mSEM 214 is provided to a classification tool 216, which is configured to compare the mSEM 214 to a predetermined threshold of expansion X % to generate a classification 218 of the blood vessel. In some embodiments, the predetermined threshold of expansion X % may be in a range of between approximately 70% and approximately 90%, between approximately 75% and approximately 85%, approximately 80%, or other similar values. If the mSEM 214 is less than the predetermined threshold of expansion X %, it is indicative that the blood vessel is an under-expanded area. If the mSEM 214 is greater than or equal to the predetermined threshold of expansion X %, it is indicative that the blood vessel is a well-expanded area. In some embodiments, the classification tool 216 may be a part of the regression model 212.

A treatment plan 220 is generated based upon the classification 218. In some embodiments, if the blood vessel is a well-expanded area then the treatment plan 220 may comprise and/or be a direct insertion of a stent into the blood vessel. In some embodiments, if the blood vessel is an under-expanded area then the treatment plan 220 may comprise a plaque modification operation (e.g., rotational and orbital atherectomy, cutting or scoring the balloon, acoustic shock wave, balloon pre-dilation, and/or the like) on the blood vessel. In some embodiments, generation of the treatment plan 220 may further take into consideration visualizations of the one or more calcification lesions. In some embodiments, after performing the plaque modification operation, a new IVOCT image of the blood vessel may be obtained and accessed by the disclosed block diagram 200 of FIG. 2.

Since the medical devices used to implement plaque modification operations are costly and carry some potential risk, the ability to accurately predict results after stenting from the pre-stent intravascular image 204 (e.g., taken before stenting) is significant when planning intervention treatment. Furthermore, once a stent is deployed in the atherosclerotic tissue, it is very difficult to increase the expansion, even with a post-dilation balloon under high pressure.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device.

In some embodiments, the computer-executable instructions may be implemented within a stent intervention expansion software package, so as to allow a health care professional to utilize the disclosed methods and/or block diagrams through the stent intervention expansion software package. In some embodiments, the stent intervention expansion software package may provide a user with a visualization of calcification lesions within a blood vessel along with a prediction of whether or not a stent may be well-expanded within the blood vessel.

FIG. 3 illustrates some embodiments of a graph 300 showing a comparison of mSEIs generated by the disclosed method and actual mSEIs measured after insertion of a stent.

Graph 300 shows case numbers along the x-axis and mSEI values along the y-axis. As shown in graph 300, an actual mSEI 302 is illustrated along with a predicted mSEI 304 for a plurality of separate cases (e.g., for 32 separate arteries). Graph 300 further illustrates a dashed horizontal line that indicates a predetermined threshold of expansion 306. The dashed horizontal line shown in graph 300 indicates that the predetermined threshold of expansion 306 is equal to 80%. In some embodiments, the actual mSEI 302 may be determined by submitting one or more pre-stent intravascular images to a Core Laboratory for independent offline analysis. In some such embodiments, analysts may be blinded to patient and procedural information and a reference lumen area may be recorded by optical coherence tomography (OCT) automated measures or calculated by tracing the luminal contour on the proximal and distal reference segments.

Of the plurality of cases shown in graph 300, a majority of the cases have good agreement between the actual mSEI 302 and the predicted mSEI 304. For example, in 27 of the 32 cases both the actual mSEI 302 and the predicted mSEI 304 are either both above the predetermined threshold of expansion 306 (indicating that a stent inserted within a corresponding artery will be well-expanded) or are both below the predetermined threshold of expansion 306 (indicating that a stent inserted within a corresponding artery will be under-expanded).

Graph 300 shows five incorrect cases 308a-308e that disagree between the actual mSEI 302 and the predicted mSEI 304. For cases 308b and 308e, the predicted mSEI is close to predetermined threshold of expansion, such that a health care professional might over-ride the prediction after reviewing the case. For cases 308a and 308d, the actual mSEI 302 was 0.72 or better, not far from the acceptable threshold of 0.8. Therefore, the disclosed method achieves good agreement with actual results over a wide range of cases.

Figure 4:
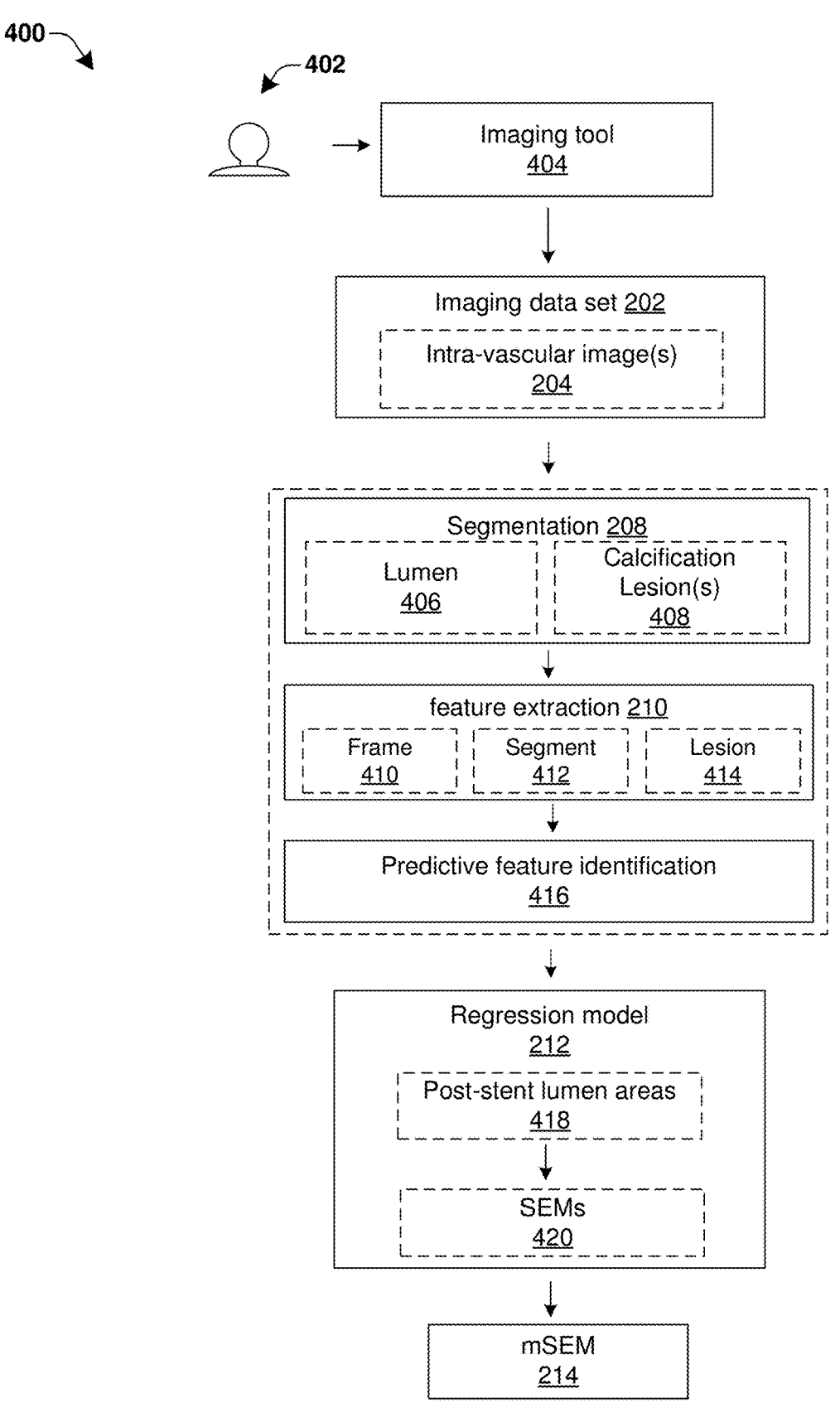
FIG. 4 illustrates some embodiments of a block diagram corresponding to a method and/or apparatus configured to generate a mSEM from a pre-stent intravascular image.

FIG. 4 illustrates some embodiments of a block diagram 400 corresponding to a method and/or apparatus configured to generate a mSEM from a pre-stent intravascular image.

As shown in the block diagram 400, an imaging data set 202 comprising one or more pre-stent intravascular images 204 is formed and/or provided. The one or more pre-stent intravascular images 204 may comprise pre-stent IVOCT images generated using an imaging tool 404 comprising an IVOCT imaging system. In some embodiments, the IVOCT imaging system may obtain the pre-stent IVOCT images by inserting a catheter into an artery of a patient 402. The catheter may comprise a probe that emits near-infrared (nIR) light with a central wavelength between approximately 1250 nanometers (nm) and approximately 1350 nm. The probe is further configured to detect backscattered light so-as-to obtain cross-sectional images of the artery. In some embodiments, the probe may rotate as it emits nIR light.

In some embodiments, the one or more pre-stent intravascular images 204 may be obtained by an imaging operation conducted using the imaging tool 404 (e.g., a C7XR FD-OCT Imaging System) after an injection of nitroglycerin (e.g., between approximately 100 grams (g) and approximately 200 g) into the patient 402. In such embodiments, optical coherence tomography (OCT) may be performed with an imaging catheter (e.g., Dragonfly OPTIS 2.7 F 135-cm). Blood clearance may be achieved by non-diluted iodine contrast using ISOVUE-370 (iopamidol injection, 370 mg iodine/mL). The one or more pre-stent intravascular images 204 may be acquired with an automated pullback at a rate of 36 mm/s using survey mode (375 frames, 75 mm), a frame rate of 180 frames/s, and an axial resolution of 20 μm.

In some embodiments, the one or more pre-stent intravascular images 204 may be subjected to quality control (QC) assessments. For example, pre-stent intravascular images may be excluded from the imaging data set 202 if the pre-stent intravascular images comprise an ostial lesion, the inability to cross lesions with an OCT catheter because of tortuosity and/or occluding thrombus, bypass graft stenosis, in-stent restenosis, chronic total occlusion, and/or the like. In some additional embodiments, pre-stent intravascular images may be excluded from the imaging data set 202 if the pre-stent intravascular images comprise lesions without either pre-stent or final OCT, without any calcium by OCT, that have been treated with plaque modification methods (e.g., rotational, laser, or orbital atherectomy or laser angioplasty), and/or the like.

The one or more pre-stent intravascular images 204 are provided to a segmentation stage 208. The segmentation stage 208 is configured to segment the one or more pre-stent intravascular images 204 to identify a lumen 406 and one or more calcification lesions 408. In some embodiments, the segmentation stage 208 may use a local difference local binary pattern (LD-LBP) operator combined with an Otsu algorithm. The LD-LBP operator is a texture operator that labels an image's pixels by thresholding a magnitude relationship between a target pixel and neighboring pixels. The Otsu algorithm then separates pixels into two classes to maximize inter-class variance.

The lumen 406 and the one or more calcification lesions 408 are provided as inputs to a feature extraction stage 210. The feature extraction stage 210 is configured to extract a plurality of features from the lumen 406 and/or the one or more calcification lesions 408. In some embodiments, thirty-nine features, from four feature groups (e.g., 12 2D lumen features, 6 3D lumen features, 12 2D calcification features, and 9 3D calcification features) may be extracted from a segmented image. First-order aggregation statistics (e.g., minimum, maximum, mean, median, SD, skewness, and kurtosis) may be obtained from some of the 39 images (e.g., for two-dimensional features in the case of the segment-based approach), to obtain a total of 238 features were obtained (e.g., 168 2D features and 69 3D features). In some embodiments, values of some of the plurality of features may be normalized between 0 and 1, while other values of features (e.g., such as lumen area) are not normalized, because the absolute area is actually important.

The plurality of features are provided to a predictive feature identification stage 416 configured perform feature reduction. In some embodiments, the feature reduction identifies predictive features, which are a subset of the plurality of features that are most determinative to calculating a post-stent lumen area, for prediction of stent under-expansion, or the like. In some embodiments, a least absolute shrinkage and selection operator (LASSO) may be used to identify the predictive features. In such embodiments, the selection method applies a shrinking (regularization) process in which it assigns weights to regression variables. LASSO shrinks the regression coefficients toward 0 to eliminate irrelevant features from a regression model. In other embodiments, an elastic net algorithm may be used to identify the predictive features.

The predictive features are provided to a regression model 212 that is configured to generate a minimum stent expansion metric (mSEM) 214 for the pre-stent intravascular image. In some embodiments, the regression model 212 may be configured to generate a plurality of post-stent lumen areas 418 for a blood vessel associated with the pre-stent intravascular image. From the plurality of post-stent lumen areas 418, a plurality of stent expansion metrics (SEMs) 420 may be calculated, and from the plurality of SEMs a mSEM 214 may be identified. In some embodiments, the regression model 212 may be configured to compute stent expansion indices (SEIs) values over an artery or a calcification lesion. The SEIs are then searched to obtain a minimum SEI (mSEI). In various embodiments, the regression model 212 may comprise a decision tree, regression support vector machine, Gaussian process regression, and ensemble models.

In various embodiments, the feature extraction stage 210 may be configured to extract the plurality of features from the lumen 406 and/or the one or more calcification lesions 408 according to a frame-based approach 410, a segment-based approach 412, or a lesion-based approach 414.

In the frame-based approach 410, a plurality of features that are used to generate a stent expansion metric for a frame are extracted from the frame. For example, during the frame-based approach 410, a first plurality of features are extracted from a first frame and a first stent expansion metric (e.g., a first SEI) associated with the first frame is calculated from the first plurality of features, a second plurality of features are extracted from a second frame and a second stent expansion metric (e.g., a second SEI) associated with the second frame is calculated from the second plurality of features, etc. In some embodiments, the plurality of features extracted using the frame-based approach 410 are two-dimensional (2D) lumen and/or calcification features.

In the segment-based approach 412, a plurality of features that are used to generate a stent expansion metric for a frame are extracted from a moving segment (e.g., a segment that moves across a calcification lesion at a stride and that comprises a plurality of frames) comprising the frame. For example, during the segment-based approach 412, a first plurality of features are extracted from a first segment comprising a first plurality of frames and a first stent expansion metric (e.g., a first SEI) associated with the first frame is calculated from the first plurality of features, a second plurality of features are extracted from a second segment comprising a second plurality of frames and a second stent expansion metric (e.g., a second SEI) associated with the second frame is calculated from the second plurality of features, etc. In some embodiments, the stent expansion metric and/or post-stent lumen area that the segment-based approach 412 determines for a frame is calculated using features that are extracted from a segment that is centered upon that frame. In some such embodiments, moving segments with different lengths (e.g., 3, 7, 15, 31, and 63 frames) are applied with a stride of 1 frame. In some embodiments, the segment lengths may be in a range of between approximately 20 frames and approximately 40 frames, between approximately 25 frames and approximately 40 frames, approximately 31 frames, or the like. Such frame lengths are sufficiently large to account for local biomechanics, while being sufficiently small to be able to operate on a relatively small number of training samples. In some embodiments, the plurality of features extracted using the segment-based approach 412 are 2D lumen features, 2D calcification features, three-dimensional (3D) lumen features, and/or 3D calcification features.

In the lesion-based approach 414, a plurality of features that are used to generate a stent expansion metric for a frame are extracted from a calcification lesion (e.g., an entire calcification lesion) comprising the frame. For example, during the lesion-based approach 414, a plurality of features are extracted from a calcification lesion comprising a plurality of frames and a first stent expansion metric (e.g., a first SEI) associated with a first frame is calculated from the plurality of features, a second stent expansion metric (e.g., a second SEI) associated with a second frame is calculated from the plurality of features, etc. In some embodiments, the plurality of features extracted using the lesion-based approach 414 are 2D lumen features, 2D calcification features, 3D lumen features, and/or 3D calcification features.

Figure 5:
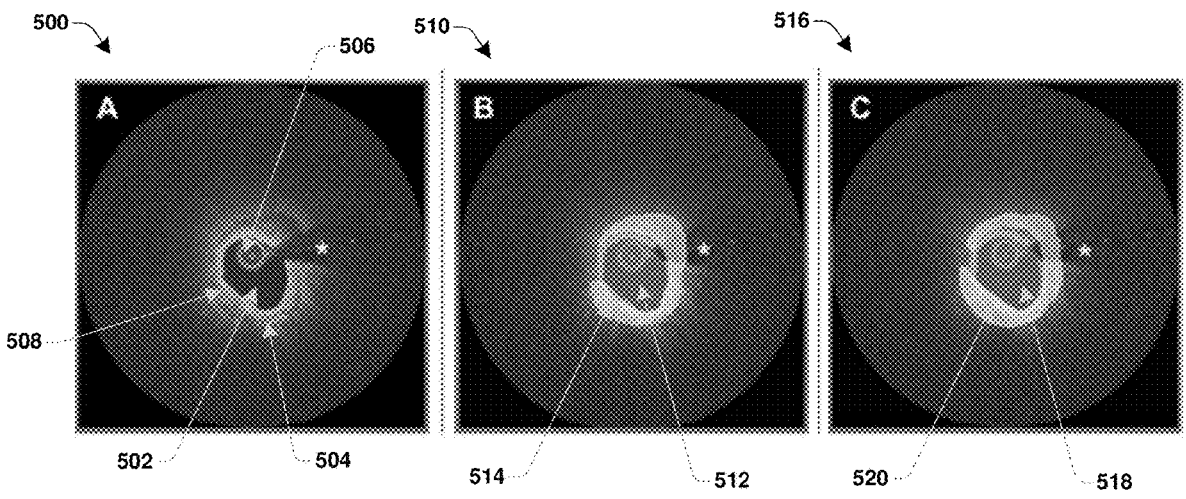
FIG. 5 illustrates some embodiments of manual and automated segmentation of intravascular optical coherence tomography (IVOCT) images.

FIG. 5 illustrates some embodiments of intravascular optical coherence tomography (IVOCT) images that have been manually and automatically segmented.

IVOCT image 500 illustrates an IVOCT image prior to segmentation. The IVOCT image 500 comprises a lumen 502 that is surrounded by a blood vessel wall 504. A catheter 506 is shown within the lumen 502. The asterisk (*) in the IVOCT image 500 indicates a guidewire shadow of the catheter 506. A calcification lesion 508 is shown between the lumen 502 and the blood vessel wall 504.

IVOCT image 510 illustrates an IVOCT image that has been subjected to manual segmentation. The manual segmentation identifies a lumen 512 and a calcification lesion 514 that wraps around the lumen 512.

IVOCT image 516 illustrates an IVOCT image that has been subjected to automated segmentation as disclosed herein (e.g., corresponding to automated segmentation performed by segmentation stage 208). The automated segmentation identifies a lumen 518 and a calcification lesion 520 that wraps around the lumen 518. Comparison between IVOCT image 510 and IVOCT image 516 shows good agreement between the manual and automated segmentation.

FIG. 6A illustrates some embodiments showing exemplary features associated with calcification lesions within for a blood vessel.

FIG. 6A shows a three-dimensional view 600 of a blood vessel 602 and a two-dimensional cross-section 606 of the blood vessel 602. As can be seen in the three-dimensional view 600 and the two-dimensional cross-section 606, calcification lesions 604 are located along a wall of the blood vessel 602. The calcification lesions 604 may have extracted features comprising a calcification length (Length), a calcification angle (θ), and/or a maximum thickness (Tmax). For example, the three-dimensional view 600 shows a calcification length (Length) of one of the calcification lesions 604 along the blood vessel 602. Two-dimensional cross-section 606 shows a calcification angle (θ) and a maximum thickness (Tmax) of one of the calcification lesions 604. In some embodiments, a lumen 607 of the blood vessel 602 may also have extracted features.

FIG. 6B illustrates some embodiments of a table 608 showing a list of features that may be extracted from a lumen and/or from calcification lesions of a blood vessel.

The table 608 illustrates 2D features 610 that may be extracted from a lumen and 2D features 612 that may be extracted from a calcification lesion. The table 608 also illustrates 3D features 614 that may be extracted from a lumen and 3D features 616 that may be extracted from a calcification lesion. In some embodiments, the 2D features, 610 and 612, may be extracted using a frame-based approach, a segment-based approach, or a lesion-based approach, while the 3D features, 614 and 616, may be extracted using a segment-based approach or a lesion-based approach. In some embodiments, subsets of the features may be used for each of the frame-based approach, the segment-based approach, and lesion-based approach.

In some embodiments, the extracted features may also comprise statistical assessments 618 of one or more of the 2D features, 610 and 612, and the 3D features, 614 and 616, shown in FIG. 6B. For example, the extracted features may comprise a mean of the area, a median of the area, etc. In some embodiments, a total of 238 features may be exacted from each frame of a pre-stent intravascular image. In other embodiments, a total number of features extracted from a pre-stent intravascular image may be more than 200 features, more than 150 features, or the like. A subset of the plurality of features may be subsequently identified as predictive features that are most determinative of post-stent lumen areas and/or of stent under-expansion within the pre-stent intravascular image. For example, 30 features of the 238 features may be identified as predictive features using a regression model (e.g., a LASSO algorithm, an elastic net algorithm, or the like).

Figure 7A:
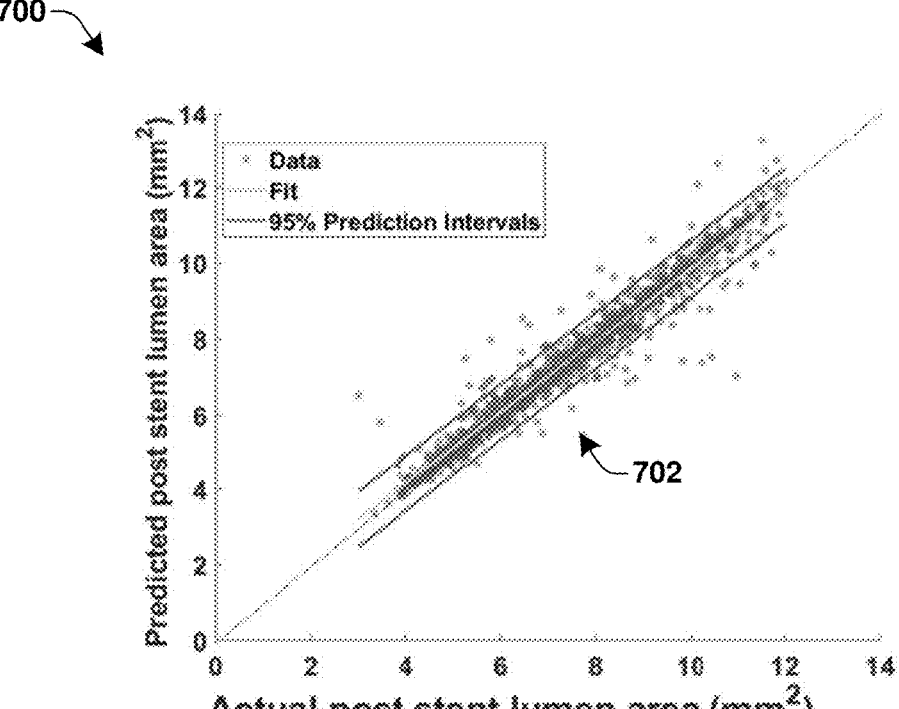
FIGS. 7A-7B illustrate some embodiments of plots showing actual stent lumen areas vs. predicted stent lumen areas determined by the disclosed method and/or apparatus.
Figure 7B:
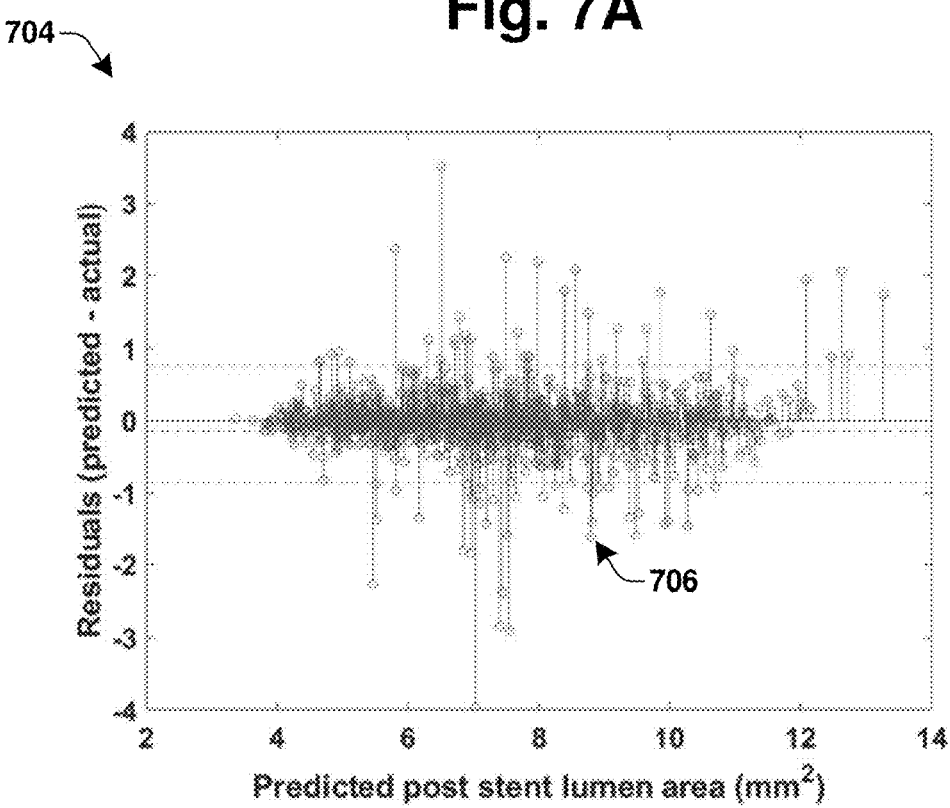

FIGS. 7A-7B illustrate some embodiments of plots showing actual (e.g., measured) post-stent lumen areas vs. predicted post-stent stent lumen areas determined by the disclosed method and/or apparatus.

FIG. 7A illustrates a scatter plot 700 showing a comparison of predicted post-stent lumen areas (shown on y-axis) vs. actual post-stent lumen areas (shown on x-axis) for a regression model that was trained using features extracted by a segment-based approach. The scatter plot 700 shows a plurality of data points 702 that correspond to both actual post-stent lumen areas and predicted post-stent lumen areas. The scatter plot 700 shows a very high similarity between the actual post-stent lumen areas and the predicted post-stent lumen areas. For example, in some embodiments the agreement between the actual post-stent lumen areas and the predicted post-stent lumen areas has a root-mean-square-error=0.4±0.02 mm², r=0.94±0.04, and p<0.0001.

FIG. 7B illustrates a residual plot 704 of predicted post-stent lumen areas for a regression model that was trained using features extracted by a segment-based approach. The residual plot 704 shows a plurality of data points 706 that correspond to predicted post-stent lumen areas. The residual plot 704 shows a very small bias (e.g., −0.1±0.7 mm²), and most of the measurements were included in the prediction interval.

FIG. 8A illustrates some embodiments of a chart 800 showing exemplary performance metrics corresponding to a disclosed regression model for different feature extraction approaches.

Chart 800 shows an accuracy 802, a sensitivity 804, a specificity 806, and an area under curve (AUC) 808 for a frame-based approach 810, a segment-based approach 812, and a lesion-based approach 814. The accuracy 802 is an ability to correctly differentiate between an under-expanded cases and well-expanded cases. In some embodiments, the accuracy 802 may be determined by calculating a proportion of a number of cases corrected identified as under-expanded and a number of cases incorrectly identified as well-expanded to all cases. The sensitivity 804 is an ability to determine under-expanded cases correctly. In some embodiments, the sensitivity 804 may be determined by calculating a proportion of cases correctly identified as under-expanded to all under-expanded cases. The specificity 806 is an ability to determine well-expanded cases correctly. In some embodiments, the specificity 806 may can be determined by calculating a proportion of cases corrected identified as well-expanded to all well-expanded cases.

In some embodiments, the best performance (root-mean-square-error=0.04±0.02 mm², r=0.94±0.04, p<0.0001) was achieved by a disclosed regression model comprising a GPR algorithm trained with a plurality of features extracted from both a lumen and a calcification lesion using a segment-based approach with a segment length of 31 frames. This may be because smaller segmental lengths do not account for the full local biomechanics, while longer segments might require more training samples. The GPR algorithm achieved an AUC of 0.85±0.02. For example, FIG. 8B illustrates some embodiments of a graph 816 having an exemplary receiver operating characteristic (ROC) curve 818 for a disclosed regression model comprising a Gaussian Process Regression (GPR) algorithm. The ROC curve 818 summarizes a performance of the GPR algorithm for predicting stent under-expansion using a segment-based approach. The AUC of 0.85 indicates that the disclosed GPR algorithm is suitably trained and reliable.

Figures 9A, 9B:
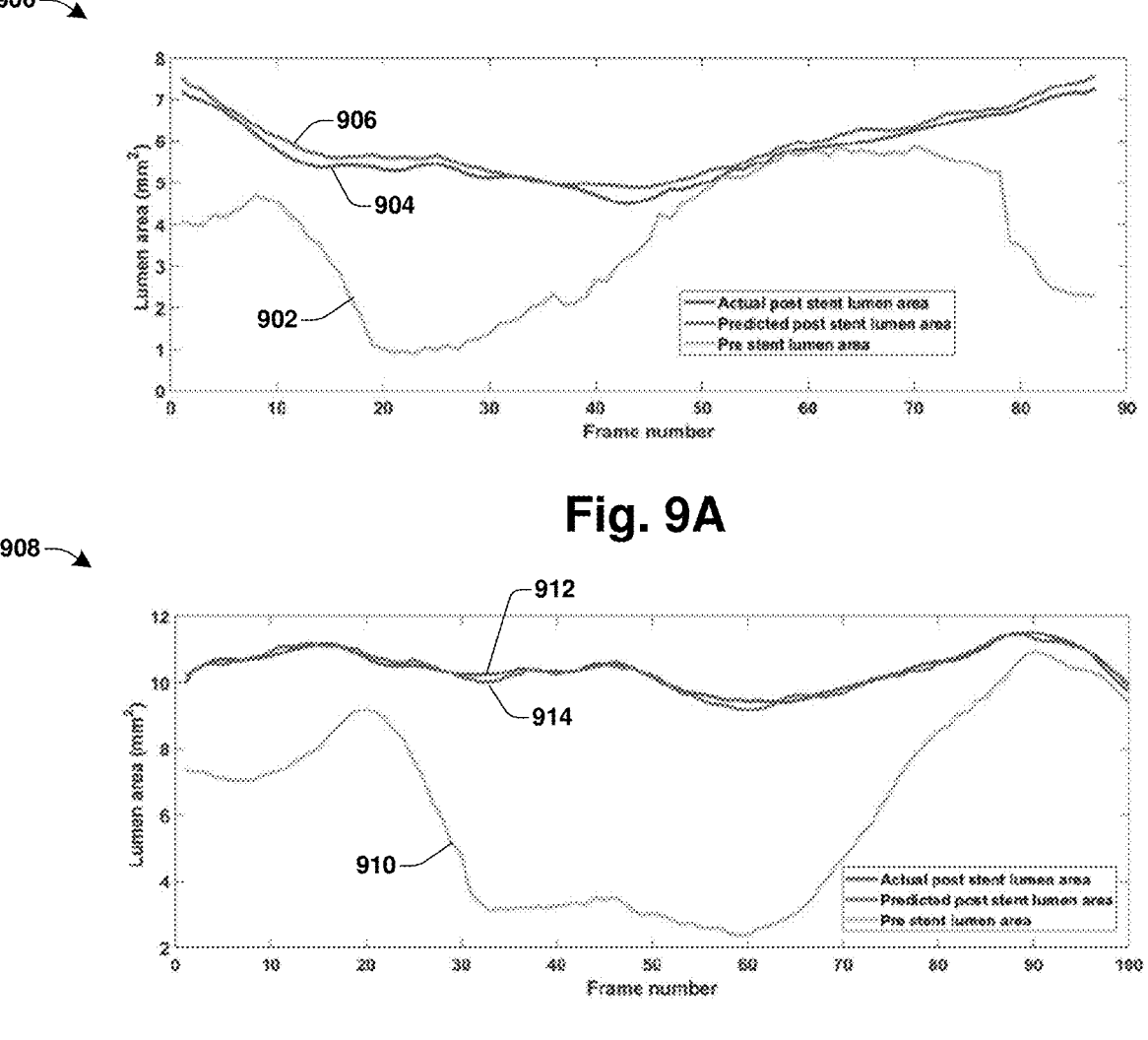
FIGS. 9A-9B illustrate some embodiments of graphs showing an actual stent lumen area vs. a predicted stent lumen area over a plurality of frames extending over a length of a blood vessel.

FIGS. 9A-9B illustrate some embodiments of graphs, 900 and 908, showing lumen areas over a plurality of frames extending over a length of a blood vessel. As illustrated by graphs, 900 and 908, the disclosed method and/or apparatus is able to achieve good agreement between predicted post-stent lumen areas and actual post-stent lumen areas along a full length of a blood vessel.

Graph 900 of FIG. 9A corresponds to an under-expanded stent area. The graph 900 shows a pre-stent lumen area 902, a predicted post-stent lumen area 904 determined from features extracted using a segment-based approach, and an actual post-stent lumen area 906 along a length of a blood vessel in IVOCT images. In the case of the under-expanded stent area shown in graph 900, there are areas in which the actual post-stent lumen area 906 was not significantly improved over a pre-stent lumen area 902 due to the presence of calcifications within the blood vessel. For example, between frame 50 and frame 70, the pre-stent lumen area 902 is substantially the same as the actual post-stent lumen area 906, indicating poor stent expansion. Because of the good agreement between the predicted post-stent lumen area 904 and the actual post-stent lumen area 906, the disclosed method and/or apparatus is able to identify under-expanded areas prior to insertion of a stent.

Graph 908 of FIG. 9B corresponds to a well-expanded stent area. The graph 908 shows a pre-stent lumen area 910, a predicted post-stent lumen area 912 determined from features extracted using a segment-based approach, and an actual post-stent lumen area 914 along a length of a blood vessel in IVOCT images. In the case of the well-expanded stent area shown in graph 908, there are areas in which the actual post-stent lumen area 906 was significantly improved over a pre-stent lumen area 902, thereby indicating good stent expansion. For example, between frame 25 and frame 80, the pre-stent lumen area 902 is significantly smaller than the actual post-stent lumen area 906, indicating good stent expansion.

Figure 10:
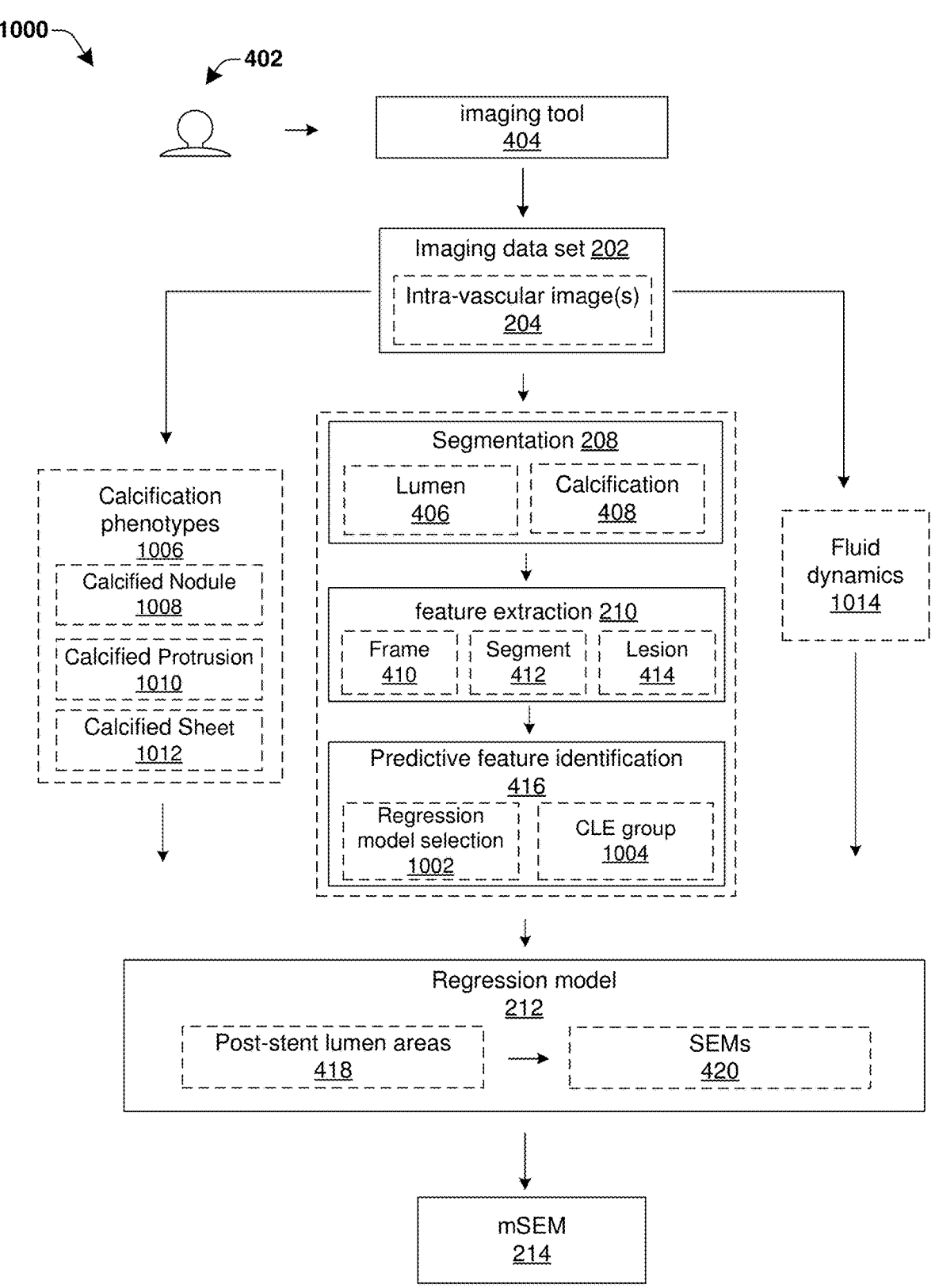
FIG. 10 illustrates some embodiments of a block diagram corresponding to a method and/or apparatus configured to generate a mSEM from a pre-stent intravascular image.

FIG. 10 illustrates some embodiments of a block diagram 1000 corresponding to a method and/or apparatus configured to generate a mSEM from a pre-stent intravascular image.

As shown in the block diagram 1000, an imaging data set 202 comprising one or more pre-stent intravascular images 204 is formed and/or provided. The one or more pre-stent intravascular images 204 may comprise IVOCT images of a blood vessel generated using an imaging tool 404 comprising an IVOCT imaging system.

The one or more pre-stent intravascular images 204 are provided to a segmentation stage 208 configured to segment the one or more pre-stent intravascular images 204 to identify a lumen 406 and one or more calcification lesions 408 within the blood vessel. The lumen 406 and the one or more calcification lesions 408 are provided to a feature extraction stage 210. The feature extraction stage 210 is configured to extract a plurality of features from the lumen 406 and/or one or more calcification lesions 408. In various embodiments, the plurality of features may be extracted according to a frame-based approach 410, a segment-based approach 412, and a lesion-based approach 414.

The plurality of features are provided to a predictive feature identification stage 416. The predictive feature identification stage 416 is configured to perform feature reduction. In some embodiments, the feature reduction is configured to identify a plurality of predictive features from the plurality of features. The plurality of predictive features are subset of the plurality of features that are most determinative to calculating a post-stent lumen area, for prediction of stent under-expansion, and/or the like. In some embodiments, the feature reduction may be performed by a regression model 1002 (e.g., a LASSO algorithm, an elastic net algorithm, or the like) configured to identify the plurality of predictive features. In some embodiments, the feature reduction may be performed manually to identify predictive features comprising a calcification lesion expansion (CLE) group 1004. The CLE group 1004 comprises intuitively important features and/or statistical assessments of features statistics that are manually selected from the plurality of features. In some embodiments, the CLE group 1004 may be subjected to a LASSO operator to identify most predictive features from the CLE group 1004.

The predictive features are provided to a regression model 212 that is configured to utilize the predictive features to determine post-stent lumen areas 418 of the blood vessel. A plurality of stent expansion metrics (SEMs) 420 are subsequently determined from the post-stent lumen areas 418 and a minimum stent expansion metric (mSEM) 214 is determined from the plurality of SEMs 420.

In some embodiments, calcification phenotypes 1006 may also be provided to the regression model 212 as independent variables to enhance a performance of the regression model 212. In some embodiments, the calcification phenotypes 1006 may comprise a calcified nodule 1008, a calcified protrusion 1010, and superficial calcified sheet 1012. It has been appreciated that adding the calcification phenotype 1006 as an independent variable to the regression model 212 improves a predictive performance of the regression model 212. In some embodiments, the calcification phenotype 1006 may be assigned by visual examination of a frame with a calcification lesion.

In some embodiments, computational fluid dynamic inputs 1014 may also be provided to the regression model 212. The computation fluid dynamic inputs 1014 determine the hemodynamic alternations following the insertion of a stent. In some embodiments, the computation fluid dynamic inputs 1014 may be implemented into the regression model 212 as a finite element method.

FIG. 11A illustrates a table 1100 showing some embodiments of exemplary features of a calcification lesion expansion (CLE) group.

The table 1100 illustrates twenty features from the CLE group. The twenty features are ranked by a LASSO algorithm for a determinative ability for prediction of stent under-expansion. As illustrated by table 1100, in some embodiments the most predictive CLE features are a calcification angle, a calcification area, a lumen area, and a percentage area stenosis.

FIG. 11B illustrates some embodiments of a bar graph 1102 showing mean AUC's for regression models trained on different feature sets (e.g., all of the plurality of extracted features, LASSO features identified from the plurality of features, features from a CLE group, and LASSO features identified from a CLE group). The mean areas under the curve (AUCs) are based off of fivefold cross validation.

Bar graph 1102 shows mean AUCs 1104 of a linear regression (LR) algorithm and a Gaussian process regression (GPR) algorithm trained using all of a plurality of features extracted from a pre-stent IVOCT image according to a segment-based approach. The mean AUCs 1104 show that a higher mean AUC is achieved using the GPR algorithm.

Bar graph 1102 further shows mean AUCs 1106 of a LR algorithm and a GPR algorithm trained using predictive features selected by operating a LASSO algorithm on the plurality of features extracted from a pre-stent IVOCT image according to a segment-based approach. The mean AUCs 1106 show that a higher mean AUC is achieved using the GPR algorithm. The mean AUCs 1106 are higher than mean AUCs 1104 illustrating that the use of the LASSO algorithm improves performance of the disclosed regression models.

Bar graph 1102 further shows mean AUCs 1108 of a LR algorithm and a GPR algorithm trained using features from a CLE group selected from the plurality of features extracted from a pre-stent IVOCT image according to a segment-based approach. In some embodiments, the CLE group may comprise the features shown in table 1100. The mean AUCs 1108 show that a higher mean AUC is achieved using the GPR algorithm. The mean AUCs 1108 are higher than mean AUCs 1106 thereby indicating that the CLE group improves performance of the disclosed regression models.

Bar graph 1102 further shows mean AUCs 1110 of a LR algorithm and a GPR algorithm trained using predictive features (e.g., a top 20 features) selected by operating a LASSO algorithm on a CLE group. The mean AUCs 1110 show that a higher mean AUC is achieved using the GPR algorithm. The mean AUCs 1110 are slightly lower than mean AUCs 1108, thereby indicating that operating feature reduction on the CLE group may not improve performance of the disclosed regression models in comparison to using the CLE group of features. Therefore, bar graph 1102 illustrates that manually selected features of a CLE group, comprising both lumen and calcification attributes, provide the best predictions of a mSEM.

Figures 12A, 12B, 12C:
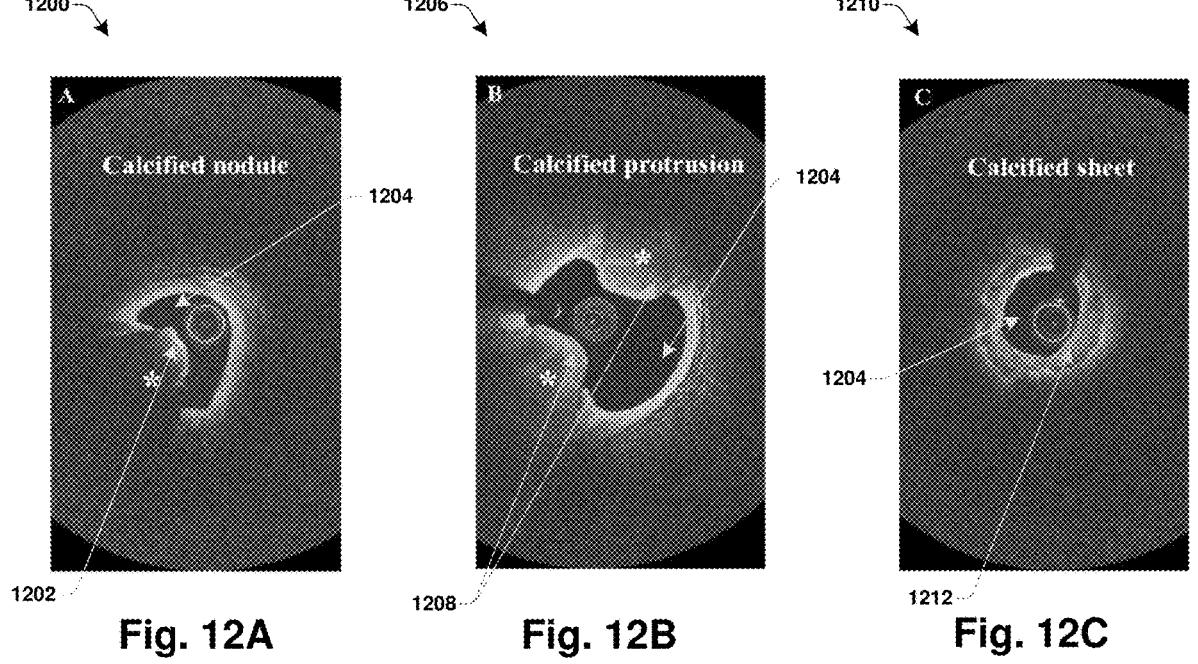
FIGS. 12A-12C illustrate some embodiments of intravascular optical coherence tomography (IVOCT) images having different calcification phenotypes.

FIGS. 12A-12C illustrate some embodiments of IVOCT images having different calcification phenotypes.

FIG. 12A illustrates an IVOCT image 1200 having a calcified nodule 1202. The calcified nodule 1202 has an erupted volcanic shape that protrudes into a lumen 1204 of a blood vessel.

FIG. 12B illustrates an IVOCT image 1206 having a calcified protrusion 1208. The calcified protrusion 1208 protrudes into a lumen 1204 of a blood vessel but without eruptive nodules.

FIG. 12C illustrates an IVOCT 1210 image having a superficial calcified sheet 1212. The superficial calcified sheet 1212 has no protrusion in the lumen.

Figures 13A, 13B:
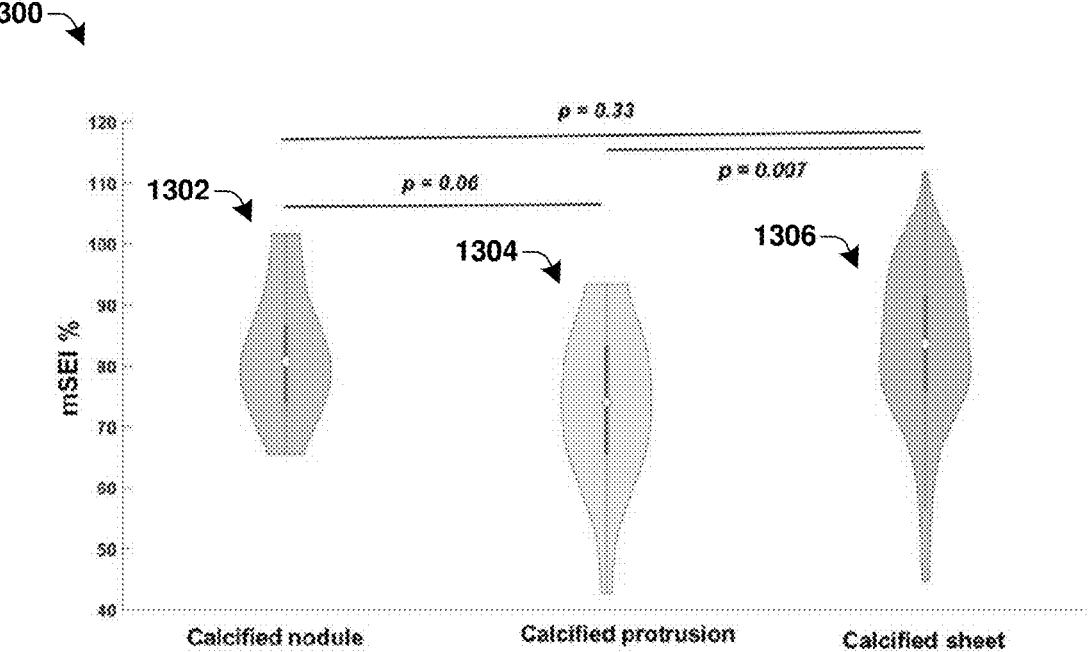
FIG. 13A illustrates some embodiments of violin plots showing distributions of mSEI values among different calcification phenotypes.
FIG. 13B illustrates some embodiments of a table showing some exemplary performance metrics corresponding to a disclosed regression model trained using different feature extraction approaches.

FIG. 13A illustrates some embodiments of a graph 1300 comprising violin plots showing distributions of mSEI values among different calcification phenotypes.

Graph 1300 comprises violin plots 1302-1306 showing distributions of minimum stent expansion index (mSEI) values for different calcification phenotypes. For example, violin plot 1302 shows a distribution of mSEI values for a calcified nodule, violin plot 1304 shows a distribution of mSEI values for a calcified protrusion, and violin plot 1306 shows a distribution of mSEI values for a calcified sheet. The calcification protrusion has a lowest mSEI median value compared to the other calcification phenotypes.

FIG. 13B illustrates some embodiments of a chart 1308 showing exemplary performance metrics corresponding to a disclosed regression model for different feature extraction approaches.

Chart 1308 shows an accuracy 802, a sensitivity 804, a specificity 806, and an area under curve (AUC) 808 for a frame-based approach 810, a segment-based approach 812, a lesion-based approach 814, and a lesion-based approach 1310 with calcification phenotypes added as an independent variable. The segment-based approach 812 with a Gaussian process regression (GPR) algorithm in combination with the CLE feature group achieved the best results. For example, the segment-based approach achieved an AUC of 0.85+−0.02. This might be because the segment-based approach 812 inherently includes many more instances of regression learning as compared with the lesion-based approach 814.

The lesion-based approach 1310 with calcification phenotypes was trained using a calcification phenotype as an independent variable. Using the calcification phenotype as an independent variable improved the AUC from 0.73±0.02 to 0.76±0.02, thereby indicating that the calcification phenotype may improve performance of the disclosed method and/or apparatus.

FIG. 14 illustrates some additional embodiments of a method 1400 of generating a machine learning model that is configured to generate a mSEM from a pre-stent intravascular image.

At act 1402, an imaging data set is formed and/or provided. The imaging data set comprises a plurality of pre-stent intravascular images and a plurality of post-stent intravascular images from a plurality of patients.

At act 1404, the imaging data set is separated into one or more training sets and one or more test sets. In some embodiments, the imaging data set may be broken into k folds of data (e.g., five folds of data). In some additional embodiments, the imaging data set may be divided into a training data set and a held-out data set. The training data set may be further divided into internal training and test sets.

At act 1406, a machine learning pipeline is trained to generate a predicted minimum stent expansion metric (mSEM) from features extracted from the plurality of pre-stent intravascular images. In some embodiments, the machine learning pipeline may operate on k−1 folds of data for training and the k fold of data for testing over a plurality of iterations (e.g., over 500 iterations). In some embodiments, each of the iterations may perform one or more operations of acts 1408-1418.

At act 1408, a segmentation is performed to identify a lumen and one or more calcification lesions within the plurality of pre-stent intravascular images within the one or more training sets.

At act 1410, a plurality of features are extracted from the lumen and/or the one or more calcification lesions.

At act 1412, predictive features are identified from the plurality of features.

At act 1414, a regression model is trained using the predictive features to determine post-stent lumen areas and/or stent expansion metrics (SEMs). In some embodiments, the SEMs may be determined for each frame of a pre-stent intravascular image by dividing a calculated post-stent lumen area of a frame by a mean of proximal and distal references $$\left( e.g., \ SEM = \frac{\text{post stent lumen area (f)} \left( mm^2 \right)}{\text{mean of proximal and distal references} \left( mm^2 \right)} * 100 \right).$$

At act 1416, a minimum stent expansion metric (mSEM) is identified from the SEMs. The mSEM is a smallest SEM of the plurality of frames of a pre-stent intravascular image.

At act 1418, the regression model is validated with the one or more test sets.

At act 1420, the regression model is validated by comparison of the mSEM to an actual mSEM measured from the plurality of post-stent intravascular images. In some embodiments, the regression model may be validated by comparing the mSEM to an actual predicted taken from a post-stent IVOCT image. To compare the predicted to the actual predicted, the images may be co-registered frame by frame prior to the comparison.

In some embodiments, the actual mSEM may be determined as a minimum of the actual SEMs calculated for each frame of a post-stent intravascular image. The actual SEMs may be determined by dividing a post-stent lumen area of a frame by a mean of proximal and distal references $$\left( e.g., \right.$$

$$\left. \text{actual } SEM = \frac{\text{post stent lumen area (f)} \left( mm^2 \right)}{\text{mean of proximal and distal references} \left( mm^2 \right)} * 100 \right).$$

Proximal and distal references may be measured at a site with a largest lumen within 5 mm proximal and distal to the stented segment.

Figure 15:
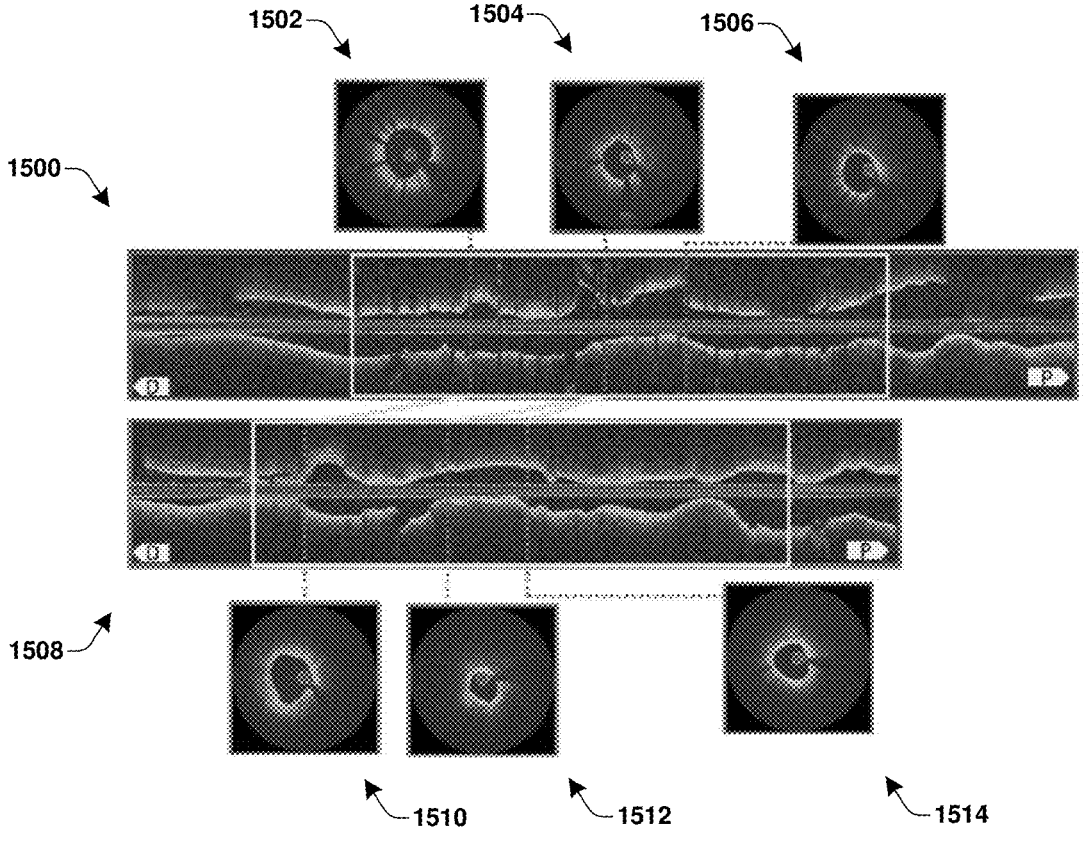
FIG. 15 illustrates some embodiments of a co-registration of pre-stent and post-stent IVOCT images.

FIG. 15 illustrates some embodiments of pre-stent and post-stent IVOCT images that are co-registered.

A pre-stent IVOCT image 1500 is illustrated along a length of a blood vessel. Cross-sectional IVOCT frames 1502-1506 are shown at different locations along the blood vessel. A post-stent IVOCT image 1508 is also illustrated along the length of the blood vessel. Cross-sectional IVOCT frames 1510-1514 are shown at different locations along the blood vessel.

A co-registration of the pre-stent IVOCT image 1500 and the post-stent IVOCT image 1508 is performed by matching landmarks (e.g., side branches and calcifications) of the two images. In some embodiments, the co-registration process may comprise a manual process by which the landmarks (e.g., side branches and calcifications) are matched up by changing the z-offset and angle of the poststent image.

In some embodiments, the cross-sectional IVOCT frames 1502-1506 of the pre-stent IVOCT image 1500 the cross-sectional IVOCT frames 1510-1514 may be co-registered frame by frame by using landmarks such as an ostium, an opening of a side branch, a coronary vein, calcifications, and/or other representative structures. Lumen and calcification labels were then used as the inputs of the feature extraction process.

Figure 16A:
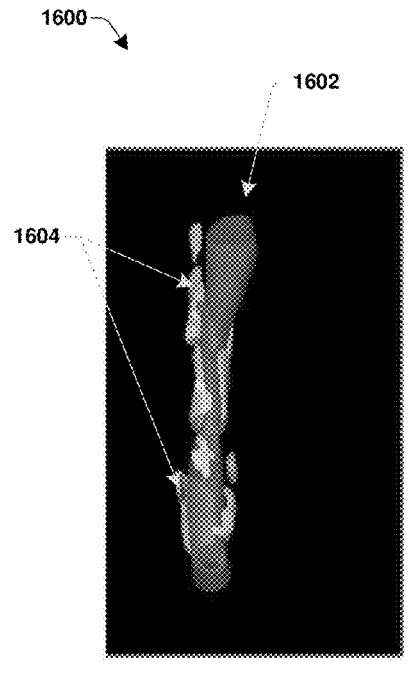
FIGS. 16A-16B illustrate some embodiments of a comparison between a predicted mSEI and an actual mSEI of an under-expanded stent area.
Figure 16B:
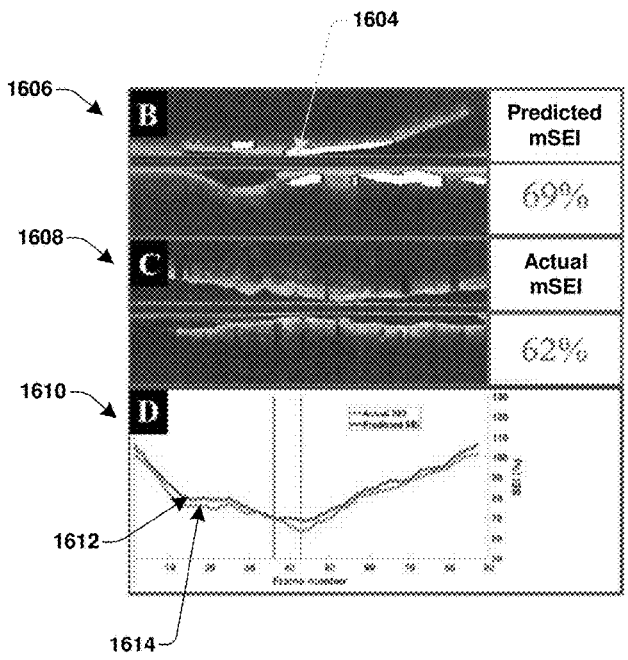

FIGS. 16A-16B illustrate some embodiments of a comparison between a predicted mSEI and an actual mSEI of an under-expanded stent area.

FIG. 16A illustrates a three-dimensional view 1600 of a blood vessel 1602 comprising a plurality of calcification lesions 1604 arranged along walls of the blood vessel 1602.

FIG. 16B illustrates a longitudinal view 1606 of the blood vessel 1602 before stenting with the plurality of calcification lesions 1604 shown in white and a longitudinal view 1608 of the blood vessel 1602 after stenting. FIG. 16B further illustrates a graph 1610 showing a comparison of a predicted mSEI 1612 calculated from features extracted from the blood vessel prior to stenting and an actual mSEI 1614 measured from the blood vessel after stenting.

The disclosed regression model predicted an mSEI of 69% for the blood vessel prior to stenting, which is close to an actual mSEI value of 62% measured from the blood vessel after stenting. Both the predicted mSEI and the actual mSEI have values indicative of under-expansion. The under-expansion is likely due to the large number of the plurality of calcification lesions 1604 preventing stent expansion. Furthermore, the curve shapes shown in graph 1610 are very similar. The vertical bars shown in graph 1610 illustrate locations corresponding to the mSEI values. The closeness of their location further suggests the predictive value of the disclosed regression model.

FIGS. 17A-17B illustrate some embodiments of a comparison between a predicted mSEI and an actual mSEI of a well-expanded stent area.

FIG. 17A illustrates a three-dimensional view 1700 of a blood vessel 1702 comprising a relatively small number of calcification lesions 1704 arranged along walls of the blood vessel 1702.

FIG. 17B illustrates a longitudinal view 1706 of the blood vessel 1702 before stenting and a longitudinal view 1708 of the blood vessel 1702 after stenting. The longitudinal view 1706 shows the calcification lesions 1704 in white. FIG. 17B further illustrates a graph 1710 showing a comparison of a predicted mSEI 1712 calculated from features extracted from the blood vessel prior to stenting and an actual mSEI 1714 measured from the blood vessel after stenting.

The disclosed regression model predicted an mSEI of 94% for the blood vessel prior to stenting, which is close to an actual mSEI value of 98% measured from the blood vessel after stenting. Both the predicted mSEI and the actual mSEI have values indicative of a well-expanded stent area. The well-expanded stent area is likely due to the small number of the plurality of calcification lesions 1704. Furthermore, the curve shapes shown in graph 1710 are very similar. The vertical bars shown in graph 1710 illustrate locations corresponding to the mSEI values. The closeness of their location further suggests the predictive value of the disclosed regression model.

Figure 18:
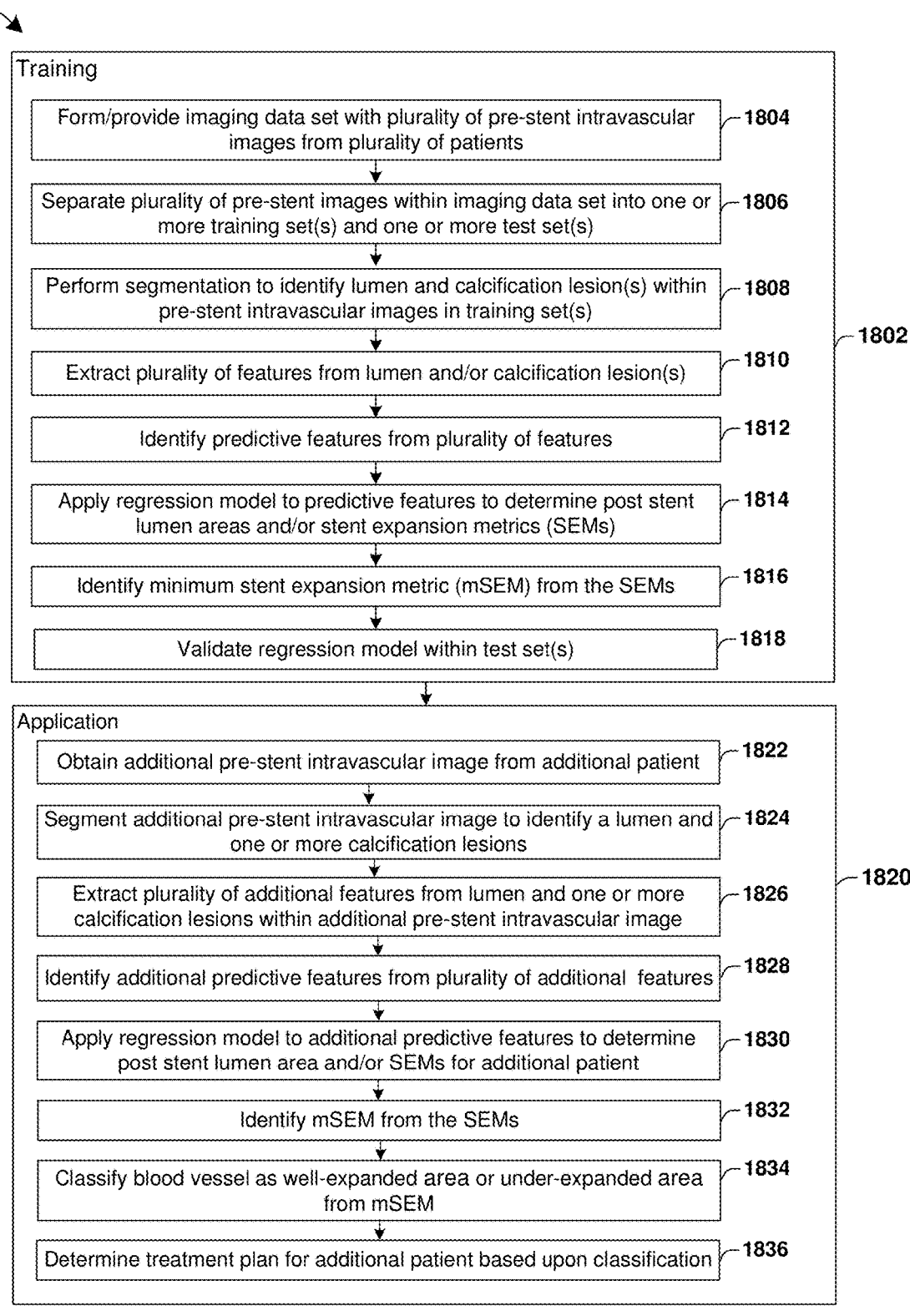
FIG. 18 illustrates some embodiments of a method of generating and applying a machine learning pipeline to generate a mSEM from a pre-stent intravascular image.

FIG. 18 illustrates some embodiments of a method of generating and applying a machine learning pipeline to generate a mSEI from a pre-stent intravascular image.

The method 1800 comprises a training phase 1802 and an application phase 1820. The training phase 1802 is configured to generate a machine learning pipeline that is able to generate a predicted mSEI for a blood vessel by using features extracted from a pre-stent intravascular image of a patient. In some embodiments, the training phase 1802 may be performed according to acts 1804-1818.

At act 1804, an imaging data set is provided and/or formed to comprise a plurality of pre-stent intravascular images from a plurality of patients.

At act 1806, the plurality of pre-stent intravascular images within the imaging data set are separated into one or more training sets and one or more test sets.

At act 1808, a segmentation is performed to identify a lumen and one or more calcification lesions within the plurality of pre-stent intravascular images.

At act 1810, a plurality of features are extracted from the lumen and/or the one or more calcification lesions.

At act 1812, predictive features are identified from the plurality of features.

At act 1814, a regression model is trained using the predictive features to determine post-stent lumen areas and/or stent expansion metrics (SEMs).

At act 1816, a minimum stent expansion metric (mSEM) is identified from the SEMs.

At act 1818, the regression model is validated using the one or more test sets.

The application phase 1820 is configured to utilize the machine learning pipeline on one or more pre-stent intravascular images, which are taken from an additional patient, to determine a predicted mSEM of a blood vessel from the additional patient.

At act 1822, an additional pre-stent intravascular image is obtained from an additional patient.

At act 1824, the additional pre-stent image is segmented to identify a lumen and one or more calcification lesions within the additional pre-stent intravascular image.

At act 1826, a plurality of additional features are extracted from the lumen and/or the one or more calcification lesions within the additional pre-stent intravascular image.

At act 1828, a subset of the plurality of additional features are identified as additional predictive features.

At act 1830, the regression model is applied to the additional predictive features to generate additional mSEMs corresponding to the blood vessel of the additional patient.

At act 1832, a mSEM is identified from the SEMs.

At act 1834, the blood vessel is classified as a well-expanded area or an under-expanded area based upon the mSEM.

At act 1836, a treatment plan is determined for the additional patient based upon the classification. If the blood vessel is classified as a well-expanded area, then the treatment plan may comprise insertion of a stent. Alternatively, if the blood vessel is classified as an under-expanded area, then the treatment plan may comprise a plaque modification strategy.

Figure 19:
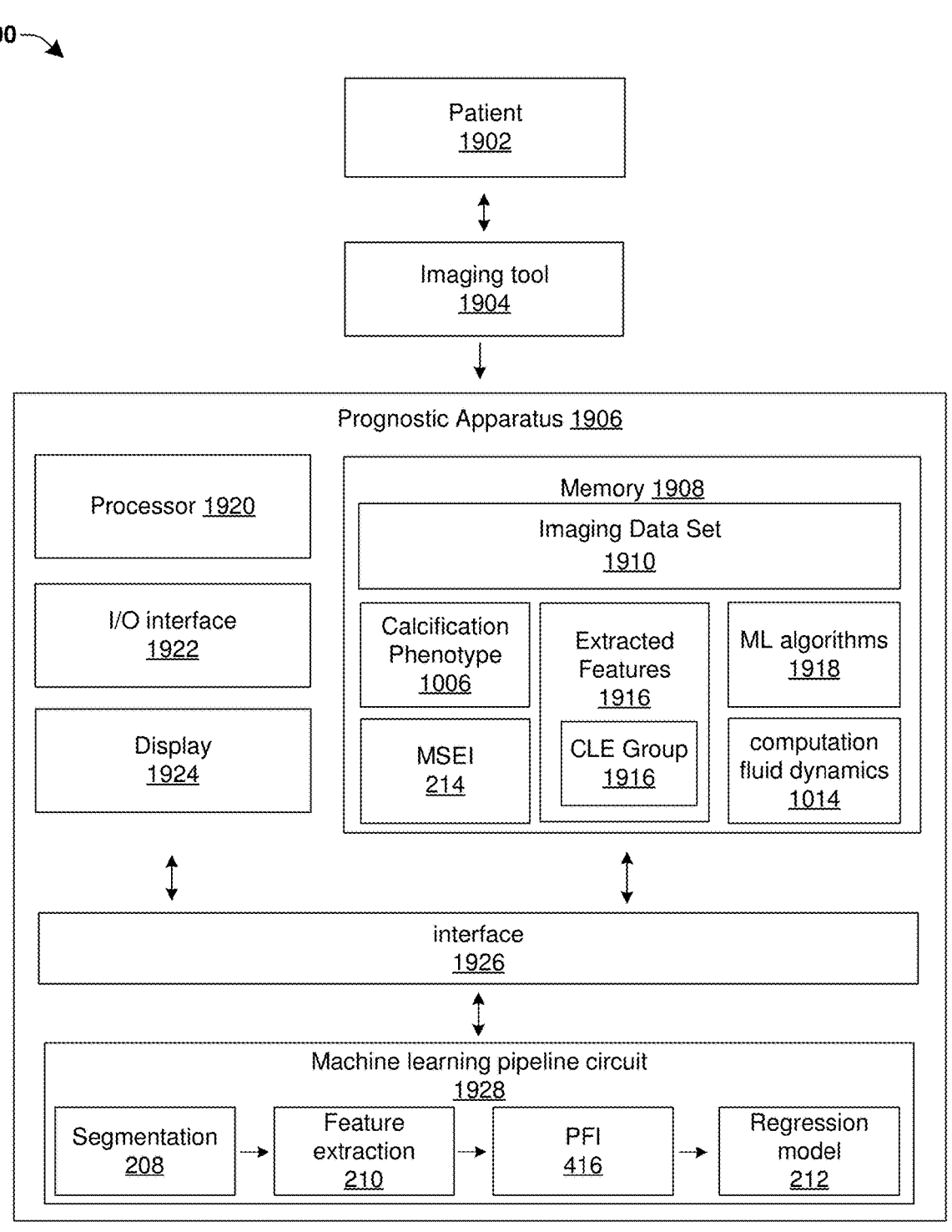
FIG. 19 illustrates some embodiments of a block diagram of an apparatus configured to determine a treatment plan from a mSEM generated from a pre-stent intravascular image.

FIG. 19 illustrates some embodiments of a block diagram of an apparatus 1900 configured to determine a treatment plan from a mSEM generated from a pre-stent intravascular image.

The apparatus 1900 comprises a prognostic apparatus 1906. The prognostic apparatus 1906 is coupled to an imaging tool 1904 that is configured to generate one or more pre-stent intravascular images of a patient 1902. In some embodiments, the imaging tool 1904 may comprise an IVOCT imaging system including a catheter that is configured to be inserted into a patient's blood vessel (e.g., artery) to obtain an IVOCT image of the blood vessel.

The prognostic apparatus 1906 comprises a processor 1920 and a memory 1908. The processor 1920 can, in various embodiments, comprise circuitry such as, but not limited to, one or more single-core or multi-core processors. The processor 1920 can include any combination of general-purpose processors and dedicated processors (e.g., graphics processors, application processors, etc.). The processor(s) 1920 can be coupled with and/or can comprise memory (e.g., memory 1908) or storage and can be configured to execute instructions stored in the memory 1908 or storage to enable various apparatus, applications, or operating systems to perform operations and/or methods discussed herein.

The memory 1908 can be configured to store an imaging data set 1910 comprising one or more pre-stent intravascular images. The one or more pre-stent intravascular images may comprise a plurality of pixels, each pixel having an associated intensity. In some additional embodiments, the imaging data set 1910 may further comprise one or more post-stent intravascular images. In some embodiments, the one or more pre-stent intravascular images may be stored in the memory 1908 as one or more training sets and/or one or more test sets (e.g., validation sets).

The prognostic apparatus 1906 also comprises an input/output (I/O) interface 1922 (e.g., associated with one or more I/O devices), a display 1924, a machine learning pipeline circuit 1928, and an interface 1926 that connects the processor 1920, the memory 1908, the I/O interface 1922, and the machine learning pipeline circuit 1928. The I/O interface 1922 can be configured to transfer data between the memory 1908, the processor 1920, the machine learning pipeline circuit 1928, and external devices, for example, the imaging tool 1904. The display 1924 is configured to output or display a mSEM generated by the prognostic apparatus 1906. In some embodiments, the display 1924 may also be configured to output an image of calcification lesions within one or more blood vessels of the one or more pre-stent intravascular images.

In some embodiments, the machine learning pipeline circuit 1928 may utilize one or more machine learning algorithms 1918 to determine a mSEM from the imaging data set 1910. In some embodiments, the machine learning pipeline circuit 1928 may comprise a segmentation stage 208, a feature extraction stage 210, a predictive feature identification stage 416, and a regression model 212. In some embodiments, the segmentation stage 208 is configured to segment the one or more pre-stent intravascular images to identify a lumen and one or more calcification lesions. In some embodiments, the feature extraction stage 210 is configured to extract a plurality of features 1916 from the lumen and/or one or more calcification lesions within respective ones of the one or more pre-stent intravascular images. The regression model 212 is configured to apply a regression model (e.g., a linear regression model, a Gaussian process regression (GPR) algorithm, etc.) to the plurality of features 1916 to determine post-stent lumen areas and/or stent expansion metrics (SEMs). A minimum stent expansion metric (mSEM) is identified from the SEMs.

In some additional embodiments, the regression model 212 may be further configured to receive a calcification phenotype 1006 stored in the memory 1908. In other additional embodiments, the regression model 212 may be further configured to receive computation fluid dynamic inputs 1014 stored in the memory 1908.

Example Use Case 1

Background: It is difficult to optimally deploy a coronary artery stent in the presence of calcifications. Building on our work in deep learning segmentation of calcifications, we created a machine learning model that uses calcification assessments to predict stent under-expansion, suggesting the need for plaque modification.

Methods: Pre-stent and post-stent intravascular optical coherence tomography image data were obtained from 110 coronary lesions. Lumen and calcifications in pre-stent images were segmented using deep learning, and numerous features per lesion were extracted. We analyzed stent expansion along the lesion, enabling frame, segmental, and whole-lesion machine learning analyses. Selected features were used to train regression models to predict the poststent lumen area and then to compute the stent expansion index (SEI). Stents with an SEI or >80% were classified as "under-expanded" and "well-expanded," respectively.

Results: The best performance (root-mean-square-error=0.04±0.02 mm2, r=0.94±0.04, p<0.0001) was achieved when we used features extracted from both the lumen and calcification to train a Gaussian process regression model for a segmental analysis over a segment length of 31 frames. Classification results were significantly improved over other approaches (AUC=0.85±0.02). Some classification errors were close calls that might be overridden by a clinician.

Conclusions: We used calcifications and lumen features to identify lesions at risk of stent under-expansion. This method provided better predictions than other methods investigated, including the previous state-of-the-art techniques. Results suggest that the use of pre-stent images can inform physicians of the need to apply plaque modification approaches.

Therefore, the present disclosure provides a fully automated method (e.g., a machine learning method) to predict stent under-expansion from a pre-stent intravascular image (e.g., intravascular optical coherence tomography (IVOCT) images).

In some embodiments, the present disclosure relates to a method of predicting stent expansion, including accessing a pre-stent intravascular image of a blood vessel of a patient; segmenting the pre-stent intravascular image to identify a lumen and a calcification lesion; extracting a plurality of features from one or more of the lumen and the calcification lesion; applying a regression model to one or more of the plurality of features to determine a minimum stent expansion metric (mSEM), the mSEM indicating how much a stent will expand after implantation; and using the mSEM to generate a classification of the blood vessel as an under-expanded area or a well-expanded area.

In other embodiments, the present disclosure relates to a non-transitory computer-readable medium storing computer-executable instructions that, when executed, cause a processor to perform operations, including accessing a pre-stent intravascular optical coherence tomography (IVOCT) image of a blood vessel of a patient; segmenting the pre-stent IVOCT image to identify a lumen and a calcification lesion; extracting a plurality of features from the lumen and the calcification lesion; identifying a plurality of predictive features from the plurality of features; applying a regression model to the plurality of predictive features to determine a minimum stent expansion metric (mSEM), the mSEM being predictive of how much a stent will expand after implantation into the blood vessel; and classifying the blood vessel as an under-expanded stent area or well-expanded stent area by comparing the mSEM to a predetermined threshold of expansion.

In yet other embodiments, the present disclosure relates to an apparatus for predicting stent expansion, including a memory configured to store a pre-stent intravascular optical coherence tomography (IVOCT) image of a blood vessel of a patient; a segmentation stage configured to segment the pre-stent IVOCT image to identify a lumen and a calcification lesion; a feature extraction stage configured to extract a plurality of features from the lumen and the calcification lesion; a regression model configured to operate upon the plurality of features to determine a minimum stent expansion metric (mSEM), the mSEM indicating how much a stent will expand within the blood vessel after implantation; and a classification tool configured to utilize the mSEM to generate a classification of the blood vessel as an under-expanded area or well-expanded area.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method of predicting stent expansion, comprising:
accessing a pre-stent intravascular image of a blood vessel of a patient;
segmenting the pre-stent intravascular image to identify a lumen and a calcification lesion;
extracting a plurality of features from one or more of the lumen and the calcification lesion;
applying a regression model to one or more of the plurality of features to determine a minimum stent expansion metric (mSEM), wherein the mSEM is determined across a plurality of frames of the pre-stent intravascular image, the mSEM indicating how much a stent will expand after implantation; and
using the mSEM to generate a classification of the blood vessel as an under-expanded area or a well-expanded area.

2. The method of claim 1, further comprising:
comparing the mSEM to a predetermined threshold of expansion, wherein the mSEM being less than the predetermined threshold of expansion indicates that the blood vessel is the under-expanded area.

3. The method of claim 2, wherein the predetermined threshold of expansion is 80% on a stent expansion index (SEI).

4. The method of claim 1, wherein the pre-stent intravascular image comprises an intravascular optical coherence tomography (IVOCT) image acquired via an IVOCT imaging system.

5. The method of claim 1, further comprising:

identifying a plurality of predictive features from the plurality of features, wherein the plurality of predictive features are indicative of one or more of a mSEM of the blood vessel and a post-stent lumen area of the blood vessel.

6. The method of claim 5, wherein the plurality of predictive features are identified using a least absolute shrinkage and selection operator (LASSO) that assigns weights to regression variables.

7. The method of claim 5, wherein one or more of the plurality of predictive features are manually selected.

8. The method of claim 1, further comprising:

applying the regression model to determine a plurality of post-stent lumen areas for the plurality of frames of the pre-stent intravascular image;

computing a plurality of stent expansion metrics (SEMs) comprising a plurality of stent expansion indices (SEIs), wherein the plurality of SEIs are determined by dividing the plurality of post-stent lumen areas for the plurality of frames by a reference area of the blood vessel; and determining a minimum stent expansion index (mSEI) from the plurality of SEIs, wherein the mSEM is the mSEI.

9. The method of claim 1, further comprising:

applying the regression model to an independent variable that correlates to a type of calcification phenotype to determine the mSEM.

10. The method of claim 1, further comprising:

extracting the plurality of features from both the lumen and the calcification lesion.

11. The method of claim 1, wherein the plurality of features comprise one or more of a two-dimensional (2D) lumen feature, a three-dimensional (3D) lumen feature, a 2D calcification feature, and a 3D calcification feature.

12. A non-transitory computer-readable medium storing computer-executable instructions that, when executed, cause a processor to perform operations, comprising:

accessing a pre-stent intravascular optical coherence tomography (IVOCT) image of a blood vessel of a patient;

segmenting the pre-stent IVOCT image to identify a lumen and a calcification lesion;

extracting a plurality of features from the lumen and the calcification lesion;

identifying a plurality of predictive features from the plurality of features, wherein the plurality of predictive features comprise a first subset of the plurality of features different from a second subset of the plurality of features, wherein the first subset of the plurality of features are more determinative of a post-stent lumen area and/or a prediction of stent expansion than the second subset of the plurality of features;

applying a regression model to the plurality of predictive features to determine a minimum stent expansion metric (mSEM), wherein the mSEM is predictive of how much a stent will expand after implantation into the blood vessel; and classifying the blood vessel as an under-expanded stent area or well-expanded stent area by comparing the mSEM to a predetermined threshold of expansion.

13. The non-transitory computer-readable medium of claim 12, wherein the plurality of features are extracted via a frame-based approach that extracts the plurality of features from a single frame of the pre-stent IVOCT image.

14. The non-transitory computer-readable medium of claim 12, wherein the plurality of features are extracted via a segment-based approach that extracts the plurality of features from a moving segment comprising a plurality of frames extending over the blood vessel.

15. The non-transitory computer-readable medium of claim 14, wherein the moving segment has a length of greater than 3 frames and a stride of 1 frame.

16. The non-transitory computer-readable medium of claim 14, wherein the mSEM that is associated with a frame is determined from features that are extracted from an area that is centered on the frame.

17. The non-transitory computer-readable medium of claim 12, wherein the plurality of predictive features are identified using an elastic net algorithm.

18. The non-transitory computer-readable medium of claim 17, wherein one or more of the plurality of predictive features are manually selected.

19. The non-transitory computer-readable medium of claim 12, wherein the operations further comprise:

applying the regression model to an independent variable that correlates to a type of calcification phenotype to determine the mSEM.

20. An apparatus for predicting stent expansion, comprising:

a memory configured to store a pre-stent intravascular optical coherence tomography (IVOCT) image of a blood vessel of a patient;

a segmentation stage configured to segment the pre-stent IVOCT image to identify a lumen and a calcification lesion;

a feature extraction stage configured to extract a plurality of features from the lumen and the calcification lesion;

a regression model configured to operate upon the plurality of features to determine a minimum stent expansion metric (mSEM), wherein the mSEM is determined across a plurality of frames of the pre-stent IVOCT image, the mSEM indicating how much a stent will expand within the blood vessel after implantation; and a classification tool configured to utilize the mSEM to generate a classification of the blood vessel as an under-expanded area or well-expanded area.

* * * * *